US006642437B1

(12) United States Patent
Lemaux et al.

(10) Patent No.: US 6,642,437 B1
(45) Date of Patent: Nov. 4, 2003

(54) PRODUCTION OF PROTEINS IN PLANT SEEDS

(75) Inventors: Peggy G. Lemaux, Moraga, CA (US); Myeong-Je Cho, Alameda, CA (US); Bob B. Buchanan, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/164,210

(22) Filed: Sep. 30, 1998

Related U.S. Application Data

(60) Provisional application No. 60/060,510, filed on Sep. 30, 1997.

(51) Int. Cl.$^7$ .......................... C12N 5/04; C12N 15/09; C12N 15/82; A01H 5/00; A01H 5/10

(52) U.S. Cl. .................. 800/287; 800/278; 800/320; 800/320.1; 800/320.3; 435/69.1; 435/69.7; 435/69.8; 435/420; 435/424; 435/430; 435/430.1; 435/431

(58) Field of Search ................ 800/278, 287, 800/320, 320.1, 320.3; 435/69.1, 69.7, 69.8, 420, 424, 430, 430.1, 431

(56) References Cited

U.S. PATENT DOCUMENTS

| | | | |
|---|---|---|---|
| 4,699,644 A | 10/1987 | Brandt et al. ................. 71/27 |
| 4,840,906 A | 6/1989 | Hunter ................. 435/240.44 |
| 5,164,310 A | 11/1992 | Smith et al. ............. 435/172.3 |
| 5,270,200 A | * 12/1993 | Sun et al. ................... 435/240 |
| 5,281,529 A | 1/1994 | Zhong et al. ........... 435/240.45 |
| 5,320,961 A | 6/1994 | Zhong et al. ........... 435/240.45 |
| 5,350,688 A | 9/1994 | Matsuno et al. ......... 435/240.5 |
| 5,403,736 A | 4/1995 | Tanimoto .............. 435/240.45 |
| 5,565,355 A | 10/1996 | Smith ................... 435/240.49 |
| 5,589,617 A | 12/1996 | Nehra et al. ................ 800/205 |
| 5,610,042 A | 3/1997 | Chang et al. ............ 435/172.3 |
| 5,641,664 A | 6/1997 | D'Halluin et al. ....... 435/172.3 |
| 5,714,474 A | 2/1998 | Van Ooijen et al. .......... 514/44 |
| 5,850,016 A | * 12/1998 | Jung et al. ................. 800/205 |

FOREIGN PATENT DOCUMENTS

| | | |
|---|---|---|
| EP | 0558676 A | 11/1992 |
| JP | 01027466 | 1/1989 |
| JP | 07213183 | 8/1995 |
| JP | 07255304 | 10/1995 |
| WO | WO 90/01551 | * 2/1990 ............. 435/172.3 |
| WO | WO 91/13993 | 9/1991 |
| WO | WO 92/20809 | 11/1992 |
| WO | WO 94/13822 | 6/1994 |
| WO | WO 94/20628 | 9/1994 |
| WO | WO 95/15392 | 6/1995 |
| WO | WO 96/04392 | 2/1996 |
| WO | WO 97/25419 | 7/1997 |
| WO | WO 97/29200 | 8/1997 |

OTHER PUBLICATIONS

Geert De Jaeger et al., "Boosting heterologous protein production in transgenic dicotyledonous seeds using Phaseolus vulgaris regulatory sequences", nature biotechnology, vol. 20, Dec. 2002, pp. 1265–1268.

Torrent et al. Plant Molecular Biology 34:139–149, Feb. 1997.*

Zheng et al. Plant Physiology 109: 777–786, 1995.*

Chaumont et al. 24:631–641, 1994.*

Cho, M.-J. et al. (1996) "Expression of Hordein Promoter-uidA Fusions in Transgenic Barley Plants" *Biotechabs* 3 (32): 103a.

Dahleen, Lynn S. (1995) "Improved plant regeneration from barley callus cultures by increased copper levels" *Plant Cell, Tissue and Organ Culture* 43: 267–269.

Forde, B. G. et al. (1985) "Nucleotide sequence of a B1 hordein gene and the identification of possible upstream regulatory elements in endosperm storage protein genes from barley, wheat and maize" *Nucleic Acids Research* 13 (20): 7327–7339.

Kimura, Tetsuya et al (1993) "The Presequence of a Precursor to the δ–Subunit of Sweet Potato Mitochondrial F1ATPase is not Sufficient for the Transport of β–Glucuronidase (GUS) into Mitochondria of Tobacco, Rice and Yeast Cells" *Plant Cell Physiol.* 34 (2): 345–355.

Sorenson, Mikael B. et al. (1996) "Hordein promoter methylation and transcriptional activity in wild–type and mutant barley endosperm" *Mol. Gen. Genet.* 250: 750–760.

Cho, M.-J. et al. (1999) "Overexpression of thioredoxin h leads to enhanced activity of starch debranching enzyme (pullulanase) in barley grain" *PNAS*, vol. 96, No. 25, 14641–14646.

Chong, D. and Langridge, W. (2000) "Expression of full-length bioactive antimicrobial human lactoferrin in potato plants" *Transgenic Research* 9: 71–78.

Haq, T., et al. (1995) "Oral immunization with a recombinant bacterial antigen produced in transgenic plants" *Science* vol. 268:714–716.

Higo, K. et al. (1993) "Expression of a chemically synthesized gene for human epidermal growth factor under the control of cauliflower mosaic virus 35S promoter in transgenic tobacco" *Biosci. Biotech. Biochem.* 57 (9): 1477–1481.

Horvath, H. et al. (2000) "The production of recombitant proteins in transgenic barley grains" *PNAS* vol. 97, No. 4: 1914–1919.

(List continued on next page.)

Primary Examiner—Elizabeth F. McElwain
Assistant Examiner—Medina A. Ibrahim
(74) Attorney, Agent, or Firm—Morrison & Foerster LLP

(57) ABSTRACT

Methods for producing proteins in plant seeds are disclosed. Expression of the protein is driven by a seed-specific promoter and the protein is preferably expressed as a fusion polypeptide that includes a signal peptide that causes the protein to accumulate in a subcellular compartment to protect the protein.

5 Claims, 7 Drawing Sheets

OTHER PUBLICATIONS

Huang, J. et al. (2001) "Expression of natural antimicrobial human lysozyme in rice grains", submitted to *Mol. Breeding*.

Jensen, L. et al. (1996) "Transgenic barley expressing a protein–engineered, thermostable (1,3–1,4)–β–glucanase during germination" *Proc. Natl. Acad. Sci. USA* vol. 93: 3487–3491.

Mason, H. et al. (1992) "Expression of hepatitis B surface antigen in transgenic plants" *Proc. Natl. Acad. Sci USA* vol. 89: 11745–11749.

Nakajima, H. et al. (1994) "Fungal and bacterial disease resistance in transgenic plants expressing human lysozyme" *Plant Cell Report* 16: 674–679.

Terashima, M. et al. (1999) "Production of functional human $\alpha^1$–antitrypsin by plant cell culture" *Appl. Microbiol. Biotechnol.* 52: 516–523.

Goldstein and Kronstad "Tissue Culture and Plant Regeneration from Immature Embryo Explants of Barley, *Hordeum vulgare*," *Theor. Appl. Genet.* 71:631–636 (1986).

Gordon–Kamm et al., "Transformation of Maize Cells and Regeneration of Fertile Transgenic Plants," *The Plant Cell* 2:603–618 (1990).

Griffin and Dibble, "High–frequency Plant Regeneration from Seed–derived Callus Cultures of Kentucky Bluegrass (*Poa pratensis* L.)," *Plant Cell Reports* 14:721–724 (1995).

Hagio et al., "Production of Fertile Transgenic Barley (*Hordeum vulgare* L.) Plant Using the Hygromycin–resistance Marker," *Plant Cell Reports* 14:329–334 (1995).

Hanzel et al., "Genotype and Media Effects on Callus Formation and Regeneration in Barley," University of Wisconsin, 27–31 (1983).

Holm et al., "Regeneration of Fertile Barley Plants from Machanically Isolated Protoplasts of the Fertile Egg Cell," *Plant Cell*, vol. 6, Abstract only (1994).

Holtorf et al., "Two Routes of Chlorophyllide Synthesis that are Differentially Regulated by Light in Barley (*Hordeum vulgare* L.)," *Proc. Natl. Acad. Sci.* 92:3254–3258 (1995).

Jahne et al., "Regeneration of Fertile Plants From Protoplasts Derived From Embryogenic Cell Suspensions of Barley (*Hordeum vulgare* L.)," *Plant Cell Reports* 10:1–6 (1991).

Jahne et al., "Regeneration of Transgenic, Microspore–derived, Fertile Barley," *Theor. Appl. Genet.* 89:525–533 (1994).

Jain et al., "An Improved Procedure for Plant Regeneration From Indica and Japonica Rice Protoplasts," *Plant Cell Reports*, vol. 14, Abstract only (1995).

Kasha et al., "Haploids in Cereal Improvement: Anther and Microspore Culture," Crop Science Dept., University of Guelph, Ontario, Canada, 213–235 (1990).

Christensen and Quail, "Ubiquitin Promoter–Based Vectors for High–Level Expression of Selectable and/or Screenable Marker Genes in Monocotyledonous Plants," *Transgenic Res.* 5:213–218 (1996).

Dahleen "Improved Plant Regeneration from Barley Callus Cultures by Increased Copper Levels," *Plant Cell, Tissue and Organ Culture* 43:267–269 (1995).

De Block et al., "Engineering Herbicide Resistance in Plants by Expression of a Detoxifying Enzyme," *The EMBO Journal* 6:2513–2518 (1987).

Fiedler and Conrad, "High–level Production and Long–term Storage of Engineered Antibodies in Transgenic Tobacco Seeds," *Bio/Technol.* 13:1090–1093 (1995).

Fletcher "Retardation of Leaf Senescence by Benzyladenine in Intact Beau Plants," *Planta* (*Berle.*) 80:1–8 (1969).

Forde et al., "Nucleotide Sequence of a $B_1$ Hordein Gene and the Identification of Possible Upstream Regulatory Elements in Endosperm Storage Protein Genes from Barley, Wheat and Maize," *Nucl. Acids Res.* 13:7327–7339 (1985).

Fromm et al., "Stable Transformation of Maize After Gene Transfer by Electroporation," *Nature* 319:791–793 (1986).

Fromm et al., "An Octopine Synthase Enhancer Element Directs Tissue:Specific Expression and Binds ASF–1, a Factor from Tobacco Nuclear Extracts," *The Plant Cell* 1:977–984 (1989).

Funatsuki et al., "Fertile Transgenic Barley Generated by Direct DNA Transfer to Protoplasts," *Theor. Appl. Genes* 91:707–712 (1995).

Ghaemi et al., "The Effects of Silver Nitrate, Colchicine, Cupric Sulfate and Genotype on the Production of Embryoids from Anthers of Tetraploid Wheat (*Triticum turgidum*)," *Plant Cell, Tissue and Organ Culture* 36:355–359 (1994).

Gless et al., "Transgenic Oat Plants Obtained at High Efficiency by Microprojectile Bombardment of Leaf Base Segments," *J. of Plant Physiology* 152:151–157 (1998).

Baillie et al., "Field Evaluation of Barley (*Hordeum vulgare* L.) genotypes Derived from Tissue Culture," *Canadian Journal of Plant Science*, 725–733 (1992).

Bhaskaran and Smith "Cell Biology and Molecular Genetics," *Crop Science* 30:1328–1337 (1990).

Bergitzer "Plant Regeneration and Callus Type in Barley: Effects of Genotype and Culture Medium," *Crop Science* 32:1108–1112(1992).

Bregitzer et al., "Plant Regeneration from Barley Callus: Effects of 2,4–dichlorophenoxyacetic acid and phenylacetic acid," *Plant Cell, Tissue and Organ Culture* 43:229–235 (1995).

Cameron–Mills, "The Structure and Composition of Protein Bodies Purified from Barley Endosperm by Silica Sol Density Gradients," *Carlsberg Res. Commun.* 45:557–576 (1980).

Cameron–Mills and Wettstein, "The Signal Peptide Cleavage Site of a $B_1$ Hordein Determined by Radiosequencing of the in vitro Synthesized and Processed Polypeptide," *Carlsberg Res. Commun.* 54:181–192 (1988).

Kott and Kasha, "Initiation and Morphological Development of Somatic Embryoids from Barley Cell Cultures," Dept. of Crop Science, University of Guelph, Ontario, Canada, 1245–1249 (1984).

Lemaux et al., "Bombardment–Mediated Transformation Methods For Barley. Bio–Rad," *US/EG Bulletin* 2007: 1–6 (1996).

Luhrs and Lorz, "Plant Regeneration in vitro from Embryogenic Cultures of Spring– and Winter–type Barley (*Hordeum vulgare* L.) Varieties," *Theor. Appl. Genet.* 75:16–25 (1987).

Marris et al., "The 5' Flanking Region Of A Barley B Hordein Gene Controls Tissue And Developmental Specific CAT Expression In Tobacco Plants," *Plant Mol. Biol.* 10:359–366 (1988).

Murakami et al., "The Bialaphos Biosynthetic Genes of *Streptomyces hygroscopicus*: Molecular Cloning and Characterization of the Gene Cluster," *Mol. Gen. Genet.* 205:42–50 (1986).

Napoli et al., "Introduction of a Chimeric Chalcone Synthase Gene into Petunia Results in Reversable Co–Suppression of Homologous Genes in trans," *The Plant Cell* 2:279–289 (1990).

Potrykus, "Gene Transfer to Plants: Assessment of Published Approaches and Results," *Annu. Rev. Plant. Physiol. Plant. Mol. Biol.* 42:205–225 (1991).

Purnhauser, "Stimulation of Shoot and Root Regeneration in Wheat *Triticum aestivum* Callus Cultures by Copper," *Cereal Research Comm.*, Abstract only (1991).

Rasmussen and Brandt, "Nucleotide Sequences of cDNA Clones for C–hordein Polypeptides," *Carlsberg Res. Commun.* 51:371–379 (1986).

Salmenkallio–Marttila et al., "Transgenic Barley (*Hordeum vulgare* L.) by Electroporation of Protoplasts," *Plant Cell Reports* 15:301–304 (1995).

Somers et al., "Fertile Transgenic Oat Plants," *Biotechnology* 10:1589–1594 (1992).

Sorenson et al., "Transcriptional and Post–transcriptional Regulation of Gene Expression in Developing Barley Endosperm," *Mol. Gen. Genet.* 217:195–201 (1989).

Sorenson et al., "Hordein Promoter Methylation And Transcriptioal Activity In Wild–Type And Mutant Barley Endosperm," *Mol. Gen. Genet.* 250:750–760 (1996).

Thompson et al., "Characterization of the Herbicide–resistance Gene bar from *Streptomyces hygroscopicus*," *The EMBO j.* 6:2519–2523 (1987).

Torbert et al., "Use of Paromomycin as a Selective Agent for Oat Transformation," *Plant Cell Reports* 635–640 (1995).

Wan and Lemaux "Generation Of Large Numbers Of Independently Transformed Fertile Barley Plants," *Plant Physiol.* 104:37–48 (1994).

Wan and Lemaux, "16 Biolistic Transformation of Microspore–derived and Immature Zygotic Embryos and Regeneration of Fertile Transgenic Barley Plants," 139–146 (1994).

Wan et al., "Type I Callus as a Bombardment Target for Generating Fertile Transgenic Maize (*Zea mays* L.)," *Planta* 196:7–14 (1995).

Zaghmout et al., "Plant Regeneration from Callus Protoplasts of Perennial Ryegrass (*Lolium perenne* L.)," *J. Plant Physiol.* 140:101–105 (1992).

Zhang et al., "Production of Multiple Shoots from Shoot Apical Meristems of Oat (*Avena sativa* L.)," *J. Plant Physiol.* 148:667–671 (1996).

Zhong et al., "Plant Regeneration Via Somatic Embryogenesis in Creeping Bentgrass (*Agrostis palustris* Huds.)," *Plant Cell Reports* 10:453–456 (1991).

Zhong et al., "In–vitro Morphogenesis of Corn (*Zea mays* L.)," *Planta* 187:483–489 (1992).

Zhong et al., "The Competence of Maize Shoot Meristems for Integrative Transformation and Inherited Expression of Transgenes," *Plant Physiol.* 110:1097–1107 (1996).

\* cited by examiner

AAGCTTTAACAACCCACACATTGATTGCAACTTAGTCCTACACAAGTTTTCCATT
CTTGTTTCAGGCTAACAACCTATACAAGGTTCCAAAATCATGCAAAAGTGATGC
TAGGTTGATAATGTGTGACATGTAAAGTGAATAAGGTGAGTCATGCATACCAAA
CCTCGGGATTTCTATACTTTGTGTATGATCATATGCACAACTAAAAGGCAACTTT
GATTATCAATTGAAAAGTACCGCTTGTAGCTTGTGCAACCTAACACAATGTCCA
AAAATCCATTTGCAAAAGCATCCAAACACAATTGTTAAAGCTGTTCAAACAAAC
AAAGAAGAGATGAAGCCTGGCTACTATAAATAGGCAGGTAGTATAGAGATCTA
CACAAGCACAAGCATCAAAACCAAGAAACACTAGTTAACACCAATCCACTATGA
AGACCTTCCTCATCTTTGCACTCCTCGCCATTGCGGCAACAAGTACGATTGCA

FIG. 3

CTTCGAGTGCCCGCCGATTTGCCAGCAATGGCTAACAGACACATATTCTGCC
AAAACCCCAGAACAATAATCACTTCTCGTAGATGAAGAGAACAGACCAAGAT
ACAAACGTCCACGCTTCAGCAAACAGTACCCCAGAACTAGGATTAAGCCGAT
TACGCGGCTTTAGCAGACCGTCCAAAAAAACTGTTTTGCAAAGCTCCAATTCC
TCCTTGCTTATCCAATTTCTTTTGTGTTGGCAAACTGCACTTGTCCAACCGATT
TTGTTCTTCCCGTGTTTCTTCTTAGGCTAACTAACACAGCCGTGCACATAGCC
ATGGTCCGGAATCTTCACCTCGTCCCTATAAAAGCCCAGCCAATCTCCACAAT
CTCATCATCACCGAGAACACCGAGAACCACAAAACTAGAGATCAATTCATTG
ACAGTCCACCGAG<u>ATGGCTAAGCGGCTGGTCCTCTTTGTGGCGGTAATCGTC</u>
<u>GCCCTCGTGGCTCTCACCACCGCT</u>

FIG. 4

PRODUCTION OF PROTEINS IN PLANT SEEDS

CROSS REFERENCE TO RELATED CASE

This application claims the benefit of co-pending U.S. provisional patent application No. 60/060,510, filed Sep. 30, 1997, which is incorporated herein by reference.

ACKNOWLEDGMENT OF GOVERNMENT SUPPORT

This invention was made with Government support under Grant CA-B-PLB-5752-14 from the U.S. Department of Agriculture. The Government has certain rights to this invention.

BACKGROUND OF THE INVENTION

Expression of Heterologous Proteins in Plant Seeds

The expression of heterologous proteins in plant seeds offers the possibility of, for example, producing large quantities of easily harvested polypeptides, and of expressing proteins that improve their grain quality. Discussions of this concept can be found in U.S. Pat. No. 5,714,474 ("Production of enzymes in seeds and their uses").

Hordein Storage Proteins

Barley seed storage proteins account for about 8 to 15% of the dry weight of the mature barley grain. The major seed storage proteins in barley are alcohol-soluble prolamines, termed hordeins, which are classified into two major groups, B and C, and two minor groups, D and γ (Shewry 1993). Depending on nitrogen levels, these four groups account for about 35 to 55% of total barley seed protein. The B-and C-hordeins account for about 70 to 80% and 10 to 20%, respectively, of the total hordein fraction, with small amounts of D- (2–4%) and γ-hordeins (not precisely determined). The B-, D- and γ-hordeins are sulfur-rich prolamines while the C hordeins are sulfur-poor prolamines (Bright and Shewry 1983). The hordeins are coordinately synthesized in the developing starchy endosperm tissue (Giese et al. 1983; Sørensen et al. 1989). They are cotranslationally transported into the lumen of the rough endoplamic reticulum, with simultaneous cleavage of the signal peptide, and are ultimately deposited into protein bodies (Cameron-Mills 1980; Cameron-Mills and von Wettstein 1980; Cameron-Mills and Madrid 1989).

Genetic analyses show that all hordeins are encoded by structural genes on chromosome 5 (1H) of barley; the Hor1, Hor2, Hor3 and Hor5 loci on chromosome 5 encode the C-, B-, D-, and γ-hordein polypeptides, respectively (Jensen et al., 1980; Shewry et al. 1980; Blake et al. 1982; Shewry et al. 1983; Shewry and Parmar 1987). The genes for B-, C- and D-hordeins have been isolated and characterized (Brandt et al. 1985; Forde et al. 1985; Rasmussen and Brandt 1986; Sørensen et al. 1996). The B- and C-hordeins are encoded by multigene families comprising 10 to 20 members while D-hordein is encoded by a single gene (Brandt et al. 1985; Rasmussen and Brandt 1986; Sørensen et al. 1996). The regulation and expression of these hordein promoters have been studied by transient expression assays (Entwistle et al. 1991; Müller and Knudsen 1993; Sørensen et al. 1996) in barley endosperm. As determined by these assays using promoter-uidA fusions, the D-hordein promoter is 3- to 5-fold more active than the B- or C-hordein promoters tested (Sørensen et al. 1996). The B-hordein promoter has also been studied using stable tobacco transformation with promoter-cat fusions (Marris et al. 1988).

Although the genes for B-, C- and D-hordeins have been isolated and characterized, their regulation and expression have been studied only in transient expression assays in barley and in stably transformed tobacco (Brandt et al., 1985; Forde et al., 1985; Marris et al., 1988 Sørensen et al., 1996).

In barley, wheat and maize, the major highly insoluble prolamin storage proteins are synthesized on polysomes closely associated with the endoplasmic reticulum (ER). (See Seeds: Physiology of Development and Germination, $2^{nd}$ ed., eds. Bewley and Black, Plenum Press, New York, 1994). Newly synthesized proteins pass through the ER membrane into the lumen, where they aggregate into small particles, which eventually form larger aggregates and protein bodies (which can be observed in electron micrographs).

In wheat, two different types of protein bodies accumulate independently within the developing endosperm: low density bodies that develop earlier and high density bodies that develop later and are derived from the ER. The high density proteins are formed when aggregation of proteins inside the lumen of the ER puts a strain on the membrane and cause it to rupture. The membrane may reform free of the protein aggregate, after an interval in which the protein body itself is not bounded by a membrane. In other cereals besides wheat and barley, such as millet, rice, maize and sorghum, the protein bodies remain as distinct membrane-bound entities even in mature seed.

SUMMARY OF THE INVENTION

The present invention provides recombinant nucleic acid molecules that employ a seed maturation specific promoter linked to a polypeptide, and particularly to a construct that also includes a signal sequence that targets a linked polypeptide to an intracellular body, such as a protein body. Such constructs may be represented as P-X or P-SS-X wherein P is a seed maturation-specific promoter, SS is a signal sequence, such as a sequence that targets a linked polypeptide to an intracellular body, and X is a polypeptide to be expressed in seed or a plant embryo. In particular embodiments, X is a non-storage protein, which is targeted to a protein storage body. Seeds expressing polypeptides of interest may be harvested at preselected times that have been found to provide greatest expression or stability of the polypeptide.

In particular embodiments, the invention provides recombinant nucleic acid molecules that employ hordein promoters, such as hordein $B_1$ and D promoters, to direct expression of polypeptides in seeds of transgenic plants, including monocot plants. In particular, the invention provides nucleic acid molecules in which a hordein signal sequence is operably linked to a nucleic acid sequence encoding the polypeptide of interest. It is shown that inclusion of a hordein signal sequence can significantly increase the levels of the expressed polypeptide in the plant seed. A wide range of polypeptides may be expressed in plant seeds in this manner, including pharmaceuticals such as insulin, interferons, erythropoietin and interleukins, and nutritional supplements.

The nucleic acid molecules provided by this aspect of the invention may be represented as Ph-hSS-X wherein Ph is a hordein promoter, hSS is a hordein signal sequence, and X is a nucleic acid molecule encoding a polypeptide (particularly a polypeptide that is not a seed storage protein), and where Ph, hSS and X are operably linked. Nucleic acid molecules lacking the hordein signal sequence may be represented as:

Ph-X.

The invention provides transgenic plants comprising these nucleic acid molecules, as well as seeds of these transgenic plants, which are useful as a source of the expressed polypeptide, or may improve the quality of the grain.

In particular embodiments of the invention, the transgenic plants provided are stably transformed monocotyledenous plant, for example cereal plants, such as barley or wheat. In particular embodiments, the invention provides stably transformed barley plants from genotypes including: Harrington, Morex, Crystal, Stander, Moravian III, Galena, Salome, Steptoe, Klages and Baronesse. The invention also provides stably transformed wheat plants from genotypes including: Anza, Karl, Bobwhite and Yecora Rojo. Most of these genotypes are not amenable to conventional transformation procedures. Accordingly, in order to enable production of stably transformed plants belonging to these genotypes, the invention also provides a transformation method that, in conjunction with the nucleic acid molecules provided, may be employed to produce the stably transformed plants. This transformation method is based upon the production of green regenerable tissues from zygotic plant embryos, and may be used to transform any monocot species, including maize, wheat, barley, rice, oat, rye, millet, sorghum, tricalate, turfgrass and forage grasses.

The transformation method comprises (a) placing an immature zygotic embryo of the selected monocot plant on plant growth medium comprising maltose as a sugar source, an auxin at a concentration of about 0.1 mg/L to about 5 mg/L, a cytokinin at a concentration of 0 mg/L to about 5 mg/L and copper at a concentration of about 0.1 $\mu$M to about 50 $\mu$M, and incubating in dim light conditions so as to form green regenerative tissue;

(b) introducing a nucleic acid molecule into the tissue by to produce transformed tissue; the nucleic acid may be either P-hSS-X,

P-X,

Ph-hSS-X, or

Ph-X wherein P is a seed maturation-specific promoter, SS is a signal sequence that tragets a polypeptide to an intracellular body (such as a protein body or vacuole), Ph is a hordein promoter (a particular seed maturation specific promoter), hSS is a hordein signal sequence, and X is a nucleic acid molecule encoding the selected polypeptide (which may be other than a seed storage protein), and where Ph, hSS and X (or Ph and X) are operably linked;

(c) incubating the transformed tissue on the plant growth medium such that green structures are observed on the transformed material;

(d) regenerating at least one transformed plant from the green structures; and (f) growing the transformed plant to produce seed.

The invention also provides seeds of stably transformed plants that express the selected polypeptide in their seed. Another aspect of the invention is a method of expressing a polypeptide in seed of a monocotyledenous plant, comprising providing a monocotyledenous plant that is stably transformed with a nucleic acid molecule of structure Ph-hSS-X, or Ph-X, and growing the plants under conditions effective to produce seed and express the polypeptide in the seed. The polypeptide can be used to improve the quality of the grain, or it can be extracted from the seed at a time of maximum expression or stability to be used for other purposes.

BRIEF DESCRIPTION OF THE DRAWINGS

FIG. 3 shows the nucleic acid sequence of the $B_1$-hordein promoter and the 57 base pair $B_1$-hordein signal sequence (underlined).

FIG. 4 shows the nucleic acid sequence of the D-hordein promoter and the 63 base pair D-hordein signal sequence (underlined).

SEQUENCE LISTING

The nucleic and amino acid sequences listed in the accompanying sequence listing are shown using standard letter abbreviations for nucleotide bases, and three letter code for amino acids. Only one strand of each nucleic acid sequence is shown, but it is understood that the complementary strand is included by any reference to the displayed strand.

Seq. I.D. No. 1 shows the nucleic acid sequence of the barley $B_1$ hordein promoter and signal sequence.

Seq. I.D. No. 2 shows the amino acid sequence of the barley $B_1$ hordein signal sequence.

Seq. I.D. No. 3 shows the nucleic acid sequence of the barley D hordein promoter and signal sequence.

Seq. I.D. No. 4 shows the amino acid sequence of the barley D hordein signal sequence.

Seq. I.D. Nos. 5–16 show PCR primers used to amplify nucleic acid molecules as described herein.

DETAILED DESCRIPTION OF THE INVENTION

1. Abbreviations and Definitions

A. Abbreviations

HMW: high molecular weight
CAT: chloramphenicol acetyl transferase
GUS: β-glucuronidase
uidA: β-glucuronidase gene
PCR: polymerase chain reaction
PEG: polyethylene glycol
MS medium: Murashige and Skoog medium
CIM: callus induction medium
IIM: intermediate-incubation medium
RM: regeneration medium
2,4-D: 2,4-dichlorophenoxyacetic acid
BAP: 6-benxylaminopurine
2iP: $N^6$-(2-isopentyl)adenine
GFP: green fluorescent protein
CaMV: cauliflower mosaic virus
rbcS: RUBISCO (D-ribulose-1,5-bisphosphate carboxylase/oxygenase) small subunit

B. Definitions

Unless otherwise noted, technical terms are used according to conventional usage. Definitions of common terms in molecular biology may be found in Lewin, *Genes V* published by Oxford University Press, 1994 (ISBN 0-19-854287-9); Kendrew et al (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the invention, the following definitions of terms are provided:

Promoter

A nucleic acid sequence that directs transcription of a protein. This includes not only molecules having the prototypical sequences, but also promoters from gene homologs. Also included are molecules that differ from the disclosed prototypical molecules by minor variations. Such variant sequences may be produced by manipulating the nucleotide sequence of a promoter using standard procedures.

Hordein Promoter

Figure 5:
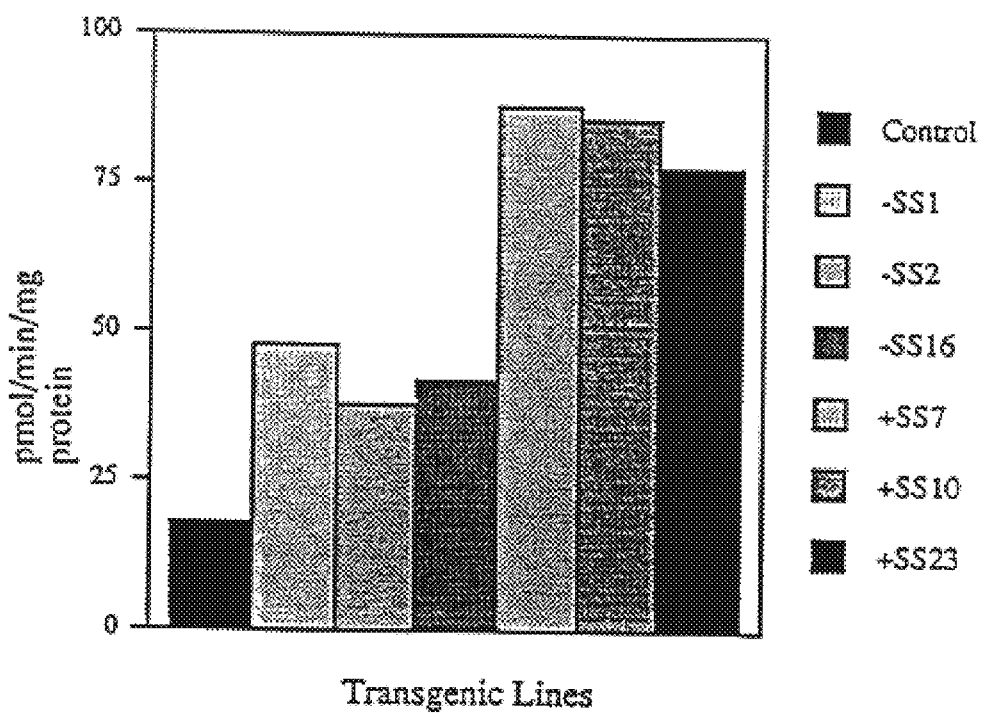
FIG. 5 is a bar graph showing GUS activity in mature barley seeds expressing constructs comprising the $B_1$-hordein promoter, the uidA gene, and the nos 3' terminator either with (+SS) or without (−SS) the $B_1$-hordein signal sequence.

A nucleic acid sequence that directs transcription of a hordein protein in seeds of a plant. While any hordein promoter may be employed for this invention, the specific examples provided describe the use of the promoter sequences from the $B_1$ and D hordein genes of barley. The nucleic acid sequences of the prototypical barley $B_1$ and D hordein genes are shown in Seq. I.D. Nos. 1 and 3, respectively as well as in FIGS. 3 and 5, respectively. The promoter region excludes those nucleotides that encode the signal sequence (the underlined sequences shown in FIGS. 3 and 4). One of skill in the art will appreciate that the length of the promoter region may also be greater or less than the sequences depicted. For example, additional 5' sequence from the hordein gene upstream region may be added to the promoter sequence, or bases may be removed from the depicted sequences. However, any hordein promoter sequence must be able to direct transcription of an operably linked sequence in plant seed. The ability of a barley hordein promoter to direct transcription of a protein in a plant seed may readily be assessed by operably linking the promoter sequence to an open reading frame (ORF) (preferably encoding a readily detectable protein) such as the GUS open reading frame, introducing the resulting construct into plants and then assessing expression of the protein in seeds of the plant, as described in detail below. A hordein promoter will typically confer seed-specific expression, meaning that expression of the protein encoded by the operably linked ORF will generally be at least twice as high (assessed on an activity basis) in seeds of the stably transfected plant compared to other tissues such as leaves. More usually, the hordein promoter will produce expression in seeds that is at least 5 times higher than expression in other tissues of the plant. In many cases, the expression of the protein in the seed will be endosperm-specific.

Functional homologs of the barley hordein promoters disclosed herein may be obtained from other plant species, such as from other monocots, including wheat, rice and corn. Specific examples of such homologs may have specified levels of sequence identity with the prototype hordein promoters (e.g., at least 60% sequence identity). the functional homologs retain hordein promoter function, i.e., retain the ability to confer seed specific expression on operably linked ORFs when introduced into plants. Accordingly, where reference is made herein to a hordein promoter, it will be understood that such reference includes not only molecules having the sequences of the prototypical sequences disclosed herein (or variations on these sequences), but also promoters from hordein gene homologs. Also included within the scope of such terms are molecules that differ from the disclosed prototypical molecules by minor variations. Such variant sequences may be produced by manipulating the nucleotide sequence of hordein promoter using standard procedures such as site-directed mutagenesis or the polymerase chain reaction.

Hordein Signal Sequence (SS)

The inventors have discovered that the inclusion of a hordein signal sequence in conjunction with a hordein promoter provides enhanced expression of certain heterologous proteins in seeds. In particular, the expression of a protein in immature seeds is greatly enhanced when the ORF encoding the protein is operably linked to both a hordein promoter and a hordein signal sequence, compared with an equivalent construct in which the hordein signal sequence is absent. While not wishing to be bound by speculation, it is proposed that the hordein signal sequence directs expression of a protein encoded by an operably linked ORF to a protected subcellular location, such as a vacuole or protein body. It is further proposed that proteins directed to such vacuoles are protected from proteolysis during certain stages of seed maturation.

The hordein signal sequence typically comprises about the first 15–25 amino acids of the hordein gene open reading frame, more usually about 18–21 amino acids. The nucleotide and amino acid sequences of the hordein signal sequences of the prototypical barley $B_1$ and D hordein genes are shown in Seq. I.D. Nos. 1–4. One of skill in the art will appreciate that while these particular signal sequences are utilized in the examples described below, the invention is not limited to these specific sequences. For example, homologous sequences may be used as effectively, as may sequences that differ in exact nucleotide or amino acid sequences, provided that such sequences result in enhanced levels of the encoded protein in immature seeds. Typically, "enhanced expression" will be expression that is about twice that observed with an equivalent construct lacking the signal sequence. Accordingly, the term "hordein signal sequence" includes not only the particular sequences shown herein, but also homologs and variants of these sequences.

Sequence Identity

The similarity between two nucleic acid sequences, or two amino acid sequences is expressed in terms of the similarity between the sequences, otherwise referred to as sequence identity. Sequence identity is frequently measured in terms of percentage identity (or similarity or homlogy); the higher the percentage, the more similar the two sequences are. Homologs of the prototype hordein promoters and hordein signal sequences will possess a relatively high degree of sequence identity when aligned using standard methods.

Methods of alignment of sequences for comparison are well known in the art. Various programs and alignment algorithms are described in: Smith and Waterman (1981); Needleman and Wunsch (1970); Pearson and Lipman (1988); Higgins and Sharp (1988); Higgins and Sharp (1989); Corpet et al. (1988); Huang et al. (1992); and Pearson et al. (1994). Altschul et al. (1994) presents a detailed consideration of sequence alignment methods and homology calculations.

The NCBI Basic Local Alignment Search Tool (BLAST) (Altschul et al., 1990) is available from several sources, including the National Center for Biotechnology Information, (NCBI, Bethesda, Md.) and on the Internet, for use in connection with the sequence analysis programs blastp, blastn, blastx, tblastn and tblastx.

Homologs of the disclosed prototype hordein signal sequences are typically characterized by possession of at least 60% sequence identity counted over the full length alignment with the amino acid sequence of the prototype using the NCBI Blast 2.0, gapped blastp set to default parameters. Proteins with even greater similarity to the reference sequences will show increasing percentage identities when assessed by this method, such as at least 70%, at least 75%, at least 80%, at least 90% or at least 95% sequence identity. Homologous hordein promoters include those from genes that encode proteins having equivalent levels of sequence identity with the $B_1$ and D hordein proteins (i.e., at least 60% and up to at least 95%).

Oligonucleotide

A linear polynucleotide sequence of up to about 100 nucleotide bases in length.

Vector

A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Transformed

A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration, and includes transient as well as stable transformants.

Isolated

An "isolated" biological component (such as a nucleic acid or protein or organelle) has been substantially separated or purified away from other biological components in the cell of the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Operably Linked

A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Recombinant

A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

cDNA (Complementary DNA)

A piece of DNA lacking internal, non-coding segments (introns) and regulatory sequences that determine transcription. cDNA is synthesized in the laboratory by reverse transcription from messenger RNA extracted from cells.

ORF (Open Reading Frame)

A series of nucleotide triplets (codons) coding for amino acids without any termination codons. These sequences are usually translatable into a peptide.

Transgenic Plant

As used herein, this term refers to a plant that contains recombinant genetic material not normally found in plants of this type and which has been introduced into the plant in question (or into progenitors of the plant) by human manipulation. Thus, a plant that is grown from a plant cell into which recombinant DNA is introduced by transformation is a transgenic plant, as are all offspring of that plant that contain the. introduced transgene (whether produced sexually or asexually).

The term "transgenic plant" also encompasses parts of plants, including fruit, seeds and pollen.

The present invention is applicable to both dicotyledonous plants (e.g., tomato, potato, soybean, cotton, tobacco, etc.) and monocotyledonous plants, including, but not limited to, graminaceous monocots such as wheat (Triticum spp.), rice (Oryza spp.), barley (Hordeum spp.), oats (Avena spp.), rye (Secale spp.), corn (*Zea mays*), sorghum and millet (Pennisettum spp). For example, the present invention can be employed with barley genotypes including, but not limited to, Morex, Harrington, Crystal, Stander, Moravian III, Galena, Salome, Steptoe, Klages, Baronesse, and with wheat genotypes including, but not limited to Yecora Rojo, Bobwhite, Karl and Anza. In general, the invention is particularly useful in cereals.

Seed Maturation

Seed maturation or grain development refers to the period starting with fertilization in which metabolizable food reserves (e.g., proteins, lipids, starch, etc.) are deposited in the developing seed, particularly in storage organs of the seed, including the endosperm, testa, aleurone layer, embryo, and scutellar epithelium, resulting in enlargement and filling of the seed and ending with seed desiccation.

Inducible

Characterized by a promoter that is upregulated by the presence or absence of a small molecule; it includes both direct and indirect inducement.

Seed Maturation Specific Promoter

A promoter induced during seed maturation, for example increased by 25% or more during seed maturation.

Signal/leader/target/transport Sequence

An N-terminal or C-terminal polypeptide sequence which is effective to co-translationally or post-translationally localize the polypeptide or protein to which it is attached to a selected intracellular vacuole or other protein storage body, chloroplast, mitochondria, or endoplasmic reticulum, or extracellular space or seed region, such as the endosperm, following secretion from the cell. An example in barley is the hordein signal sequence, but other examples include signal sequences in maize (Bagga et al., *Plant Cell* 9:1683–1696, 1997 in which coexpression of the maize delta-zein and beta-zein genes results in stable accumulation of delta-zein in endoplasmic reticulum-derived bodies formed by beta-zein; Torrent et al., *Plant Molecular Biology* 34:139–149, 1997 in which lysine-rich modified gamma-zeins accumulate in protein bodies of transiently transformed maize endosperms); in rice (Wu et al., *Plant Journal* 14:673–683, 1998 in which the GCN4 motif is essential for endosperm-specific gene expression, and is activated by Opaque-2, in transgenic rice plants; Zheng et al., *Plant Physiology* 109:777–786, 1995 in which bean beta-phaseolin was expressed in transgenic rice endosperm, primarily in the vacuolar type-II protein bodies near the aleurone layer); in wheat (Grimwade et al., *Plant Molecular Biology* 30:1067–1073, 1996 in which expression patterns of genes coding for wheat gluten proteins were described); in tobacco with legumin (Conrad et al., *Journal of Plant Physiology* 152:708–711, 1998) which discloses large-scale production of pharmaceutical proteins in transgenic tobacco plants using two seed-specific Vicia faba promoters from the legumin B4 so that the product was retained in the endoplasmic reticulum); and soy engineered using the lectin gene (Takaiwa et al., *Plant Science* 111:39–49, 1995 in which soybean glycinin genes, transcriptionally fused to an endosperm-specific promoter of the rice storage protein glutelin gene, were introduced into the tobacco genome via Agrobacterium-mediated transformation, and were expressed specifically in the cotyledon and embryo of maturing soybean seed).

Terminal Processing or Termination Sequence

A DNA sequence located 3' to the coding region which causes RNA polymerase to terminate transcription of a gene, and dissociate from the DNA. An example is the nos 3' terminator. A terminator may also occur during post-transcription processing of mRNA in vivo, as indicating where a precursor mRNA molecule should be cleaved to yield a mature mRNA species which will be translated. A segment containing a terminal-processing signal can be obtained by comparing cDNA encoding an endosperm-expressed product coding for the same product, thereby to identify the 3' terminus of the cDNA. By isolating a genomic DNA segment comprising 50 to 100 base-pairs on either side of the 3' terminus, one is assured of obtaining a segment with the terminal-processing signal.

Protein Body

Intracellular structure containing proteins within a unit membrane structure. In some cases this structure is referred to as a vacuole.

Seed Storage Protein

An endogenous plant protein which is synthesized and accumulated during seed maturation, stored in the dry grain, and mobilized during maturation. Such proteins are often stored in a protein body in a plant seed. Examples of such storage proteins include arachin, avenin, cocosin, conarchin, concocosin, conglutin, conglycinin, convicine, crambin, cruciferin, cucurbitin, edestin, excelesin, gliadin, gluten, glytenin, glycinin, helianthin, hordein, kafirin, legumin, napin, oryzin, pennisetin, phaseolin, psophocarpin, secalin, vicilin, vicine and zein.

II. Seed-Specific Expression of Proteins Using Hordein Promoter/Hordein Signal Sequence Constructs a. Constructs The present invention provides recombinant constructs that are suitable for obtaining high level expression of a specified polypeptide in plant seeds. The constructs may be generally represented as Ph-hSS-X, wherein Ph is a hordein promoter, hSS is a hordein signal sequence, and X is a nucleic acid molecule encoding the specified polypeptide. Each of these three components is operably linked to the next, i.e., the hordein promoter is linked to the 5' end of the sequence encoding the hordein signal sequence, and the hordein signal sequence is operably linked to the X sequence. The construct will usually also contain 3' regulatory sequences, such as the Nos 3' region.

The characteristics of hordein promoters and signal sequences are described above. The B1 and D hordein genes are described in Brandt et al. (1985) and Sørensen et al. (1996). When the promoter is Ph, the polypeptide "X" may be any polypeptide except for a hordein polypeptide, and in particular embodiments is other than a seed storage protein, or even a seed specific protein. Polypeptides X that may be expressed in plant seeds as described herein, as part of a P-X, P-SS-X, Ph-X or Ph-SS-X construct include non seed specific proteins such as human therapeutic proteins (e.g., erythropoietin, tissue plasminogen activator, urokinase and prourokinase, growth hormones, cytokines, factor VIII, epoetin-α, granulocyte colony stimulating factor, antibodies, vaccines, etc.), or more plant specific proteins such as enzymes for starch biosynthesis (e.g., ADP glucosepyrophosphorylase, EC 2.7.7.27; starch synthase, EC 2.4.1.21; and branching enzyme, R,Q) and seed specific proteins, such as those conferring enhanced nutritional value on the seeds. Nucleic acids encoding such proteins are well known in the art. The coding region for such a protein may be modified such that it more closely conforms to the preferred codon usage bias for a particular host cell.

Other heterologous proteins encoded by the chimeric gene include polypeptides that form immunologically active epitopes, and enzymes that catalyze conversion of intracellular metabolites, with the consequent build-up of selected metabolites in the cells.

The expression cassette or chimeric genes in the transforming vector typically have a transcriptional termination region at the opposite end from the transcription initiation regulatory region. The transcriptional termination region may normally be associated with the transcriptional initiation region from a different gene. The transcriptional termination region may be selected, particularly for stability of the mRNA, to enhance expression. Illustrative transcriptional termination regions include the NOS terminator from Agrobacterium Ti plasmid and the rice α-amylase terminator.

Polyadenylation tails are also commonly added to the expression cassette to optimize high levels of transcription and proper transcription termination, respectively.

Standard molecular biology methods, such as the polymerase chain reaction may be employed to produce these constructs.

b. General Principles of Plant Transformation

Introduction of the Ph-hSS-X construct into plants is typically achieved using standard techniques. The basic approach is to clone the construct into a transformation vector which is then introduced into plant cells by one of a number of techniques (e.g., electroporation) and progeny plants containing the introduced construct are selected. Preferably all or part of the transformation vector will stably integrate into the genome of the plant cell. That part of the transformation vector which integrates into the plant cell and which contains the introduced Ph-hSS-X sequence (the introduced "transgene") may be referred to as the recombinant expression cassette.

Selection of progeny plants containing the introduced transgene may be made based upon the detection of protein X expression or seeds, or upon enhanced resistance to a chemical agent (such as an antibiotic) as a result of the inclusion of a dominant selectable marker gene incorporated into the transformation vector.

Successful examples of the modification of plant characteristics by transformation with cloned nucleic acid sequences are replete in the technical and scientific literature. Selected examples, which serve to illustrate the knowledge in this field of technology include:

U.S. Pat. No. 5,571,706 ("Plant Virus Resistance Gene and Methods")
U.S. Pat. No. 5,677,175 ("Plant Pathogen Induced Proteins")
U.S. Pat. No. 5,510,471 ("Chimeric Gene for the Transformation of Plants")
U.S. Pat. No. 5,750,386 ("Pathogen-Resistant Transgenic Plants")
U.S. Pat. No. 5,597,945 ("Plants Genetically Enhanced for Disease Resistance")
U.S. Pat. No. 5,589,615 ("Process for the Production of Transgenic Plants with Increased Nutritional Value Via the Expression of Modified 2S Storage Albumins")
U.S. Pat. No. 5,750,871 ("Transformation and Foreign Gene Expression in Brassica Species")
U.S. Pat. No. 5,268,526 ("Overexpression of Phytochrome in Transgenic Plants")
U.S. Pat. No. 5,780,708 ("Fertile Transgenic Corn Plants")
U.S. Pat. No. 5,538,880 ("Method For Preparing Fertile Transgenic Corn Plants")
U.S. Pat. No. 5,773,269 ("Fertile Transgenic Oat Plants")
U.S. Pat. No. 5,736,369 ("Method For Producing Transgenic Cereal Plants")
U.S. Pat. No. 5,610,042 ("Methods For Stable Transformation of Wheat").

These examples include descriptions of transformation vector selection, transformation techniques and the construction of constructs designed to express an introduced transgene. In light of the foregoing and the provision herein of Ph-hSS-X constructs, it is thus apparent that one of skill in the art will be able to introduce these constructs into plants in order to produce plants that express the desired protein (X) in their seeds.

c. Plant Types

The Ph-hSS-X constructs of the present invention may be usefully expressed in a wide range of higher plants to obtain seed specific expression of selected polypeptides. The invention is expected to be particularly applicable to monocotyledonous cereal plants including barley, wheat, rice, rye, maize, tricalate, millet, sorghum, and oat forage and turf grasses. In particular, the transformation methods described herein will enable the invention to be used with genotypes of barley including Morex, Harrington, Crystal, Stander, Moravian III, Galena, Golden Promise, Steptoe, Klages and Baronesse, and commercially important wheat genotypes including Yecora Rojo, Bobwhite, Karl and Anza.

The invention may also be applied to dicotyledenous plants, including, but not limited to, soybean, cotton, beans, rape/canola, alfalfa, flax, sunflower, safflower, brassica, cotton, flax, peanut, clover; vegetables such as lettuce, tomato, cucurbits, cassava, potato, carrot, radish, pea, lentils, cabbage, cauliflower, broccoli, Brussels sprouts, peppers; and tree fruits such as citrus, apples, pears, peaches, apricots, and walnuts.

d. Vector Construction

A number of recombinant vectors suitable for stable transfection of plant cells or for the establishment of transgenic plants have been described including those described in Pouwels et al., (1987), Weissbach and Weissbach, (1989), and Gelvin et al., (1990). Typically, plant transformation vectors include one or more ORFs under the transcriptional control of 5' and 3' regulatory sequences and a dominant selectable marker. The selection of suitable 5' and 3' regulatory sequences for constructs of the present invention is discused above. Dominant selectable marker genes that allow for the ready selection of transformants include those encoding antibiotic resistance genes (e.g., resistance to hygromycin, kanamycin, bleomycin, G418, streptomycin or spectinomycin) and herbicide resistance genes (e.g. phosphinothricin acetyltransferase).

e. Transformation and Regeneration Techniques

Methods for the transformation and regeneration of both monocotyledonous and dicotyledonous plant cells are known, and the appropriate transformation technique will be determined by the practitioner. The choice of method will vary with the type of plant to be transformed; those skilled in the art will recognize the suitability of particular methods for given plant types. Suitable methods may include, but are not limited to: electroporation of plant protoplasts; liposome-mediated transformation; polyethylene glycol (PEG) mediated transformation; transformation using viruses; micro-injection of plant cells; micro-projectile bombardment of plant cells; vacuum infiltration; and *Agrobacterium tumefaciens* (AT) mediated transformation. Typical procedures for transforming and regenerating plants are described in the patent documents listed at the beginning of this section.

f. Selection of Transformed Plants

Following transformation and regeneration of plants with the transformation vector, transformed plants are usually selected using a dominant selectable marker incorporated into the transformation vector. Typically, such a marker will confer antibiotic or herbicide resistance on the seedlings of transformed plants, and selection of transformants can be accomplished by exposing the seedlings to appropriate concentrations of the antibiotic.

After transformed plants are selected and grown to maturity to allow seed set, the seeds can be harvested and assayed for the expression of the expressed "X" polypeptide.

III. Use of Seed-Expressed Polypeptides

Cells transformed as above are used to regenerate plants, and seeds from the plants are allowed to mature, typically in the field, with consequent production of heterologous protein in seeds.

Polypeptides expressed in seed using the methods described herein may be harvested from the seed at any point after expression of the protein-has commenced. That is, it is not necessary for the seeds to have undergone maturation prior to harvesting. The expressed proteins may be isolated from the seeds, if desired, by conventional protein purification methods. For example, the seed can be milled, then extracted with an aqueous or organic extraction medium, followed by purification of the extracted foreign protein. Alternatively, depending on the nature of the expressed protein and the intended use, the seeds may be used directly without purification of the expressed protein.

There are differences in accumulation patterns of different polypeptides or fractions within the seed. For example, GUS expression with the GPDhGN-6-9-6 transgenic line has been found to peak at about 20 days, whereas GUS expression in the GPBhGN-4-34-7-1-2 line is higher at 10–14 days than at 20 days. Thus differential expression patterns can be monitored, and peptides extracted at times of expected peak expression.

Where the protein has been targeted to a selected intracellular body, such as a protein storage vacuole, plastid, or mitochondria, the intracellular body can first be fractionated from a seed-cell homogenate, then further fractionated to obtain the desired protein in enriched or purified form.

IV. Alternative Expression Systems

The expression systems described in the Examples below are based on the barley hordein promoter/signal sequence system. However, one of skill in the art will appreciate that the invention is not limited to this particular system. Thus, in other embodiments, other promoters and other signal sequences may be employed to express polypeptides in seed of plants, particularly cereals.

Constructs employing such sequences may be represented as:

P-X or P-SS-X, wherein X is the polypeptide to be expressed (which may be a nonplant or non-seed specific or non-plant storage protein), P is a seed maturation-specific promoter, SS is a signal sequence, such as a sequence that targets a linked polypeptide to an intracellular body, such as a protein body in which the protein is stored.

The promoter P may be a seed-specific (including, but not limited to, endosperm-specific or embryo-specific) promoter. A promoter is seed specific if its expression in a seed of a plant is at least ten-fold greater than in leaves or roots of the plant when the promoter is most actively expressed during seed maturation, and is considered endosperm-specific if its expression in the endosperm is at least five-fold greater than in other tissues of a seed when the promoter is most actively expressed during seed development. Any well-known seed-specific transcription control element or promoter can be used in addition to barley hordein promoters, including, but not limited to, promoters from any gene encoding a seed storage protein, such as well-known promoters from genes encoding: a rice glutelin, oryzin, or prolamine; wheat gliadin or glutenin; maize zein or glutelin; oat glutelin; sorghum kafirin; millet pennisetin; or rye secalin, for example.

In order to increase the levels of an expressed polypeptide, it is preferable for the protein to accumulate in a subcellular location in which the polypeptide is protected from proteolysis (that is, proteolytic degradation of the polypeptide is reduced by at least 10%, more typically by 25%, and most typically by at least 50%). As a result, it is preferred to express the polypeptide as a fusion polypeptide comprising, in the same reading frame, the coding sequence for the polypeptide and the coding sequence for a peptide (referred to interchangeably as a signal, leader, transport, or targeting sequence or peptide) that causes the fusion protein to be co-translationally or post-translationally directed to a subcellular compartment or to be secreted from the cell. Preferably, the signal peptide causes the fusion protein to be directed to a protected subcellular compartment such as the vacuole. For example, a signal peptide that causes a protein to accumulate in a vacuole may be referred to as a vacuolar targeting peptide. The signal peptide is preferably located at the 5'- or 3'-end of the fusion protein. Any well-known leader or signal peptide that causes co-translational or post-translational localization of an expressed polypeptide to such a protected subcellular compartment can be used, in addition to barley hordein signal peptides. Other such signal peptides and leaders include, but are not limited to, a signal peptides from a monocot seed-specific genes such as: a glutelin (e.g., from rice, wheat, corn, oat, etc.), prolamine, hordein, gliadin, glutenin, zein, albumin, globulin, ADP glucosepyrophosphorylase, starch synthase, branching enzyme, Em, and lea. Another exemplary class of signal sequences are sequences effective to promote secretion of polypeptides from aleurone cells during seed germination, including the signal sequences associated with α-amylase, protease, carboxypeptidase, endoprotease, ribonuclease, Dnase/Rnase, (1-3)-β-glucanase, (1-3)(1-4) β-glucanase, esterase, acid phosphatase, pentosamine, endoxylanase, β-xylopyranosidase, arabinofuranosidase, α-glucosidase, (1-6) α-glucanase, peroxidase and lysophospholipase.

The signal peptide may be cleaved by cellular enzymes co-translationally or post-translationally. Alternatively, if the signal peptide is not cleaved, the fusion polypeptide may be cleaved after purification of the fusion polypeptide, if desired. For this purpose, an amino-acid sequence may be introduced between the signal peptide and the heterologous protein to facilitate enzymatic or chemical cleavage to remove the signal peptide.

The following examples serve to illustrate the invention.

EXAMPLES

Example 1

Generation of Ph-hSS-X Constructs

The polymerase chain reaction was employed to produce constructs for introduction into plants. The methods used were variations of those described by Higuchi et al. (1990), Horton et al. (1990), Pont-Kingdon et al. (1994) and Lefebvre et al. (1995). The methods were employed to produce a Ph-hSS-X construct in which Ph was the barley endosperm-specific $B_1$-hordein promoter, hSS was the barley $B_1$-hordein signal sequence and X was the *Escherichia coli* β-glucuronidase (uidA; gus) ORF. The construct further included the nopaline synthase (nos) 3' terminator. Two PCR construction methods were used: a four primer method illustrated in FIG. 1A, and a three primer method illustrated in FIG. 1B.

All PCR reactions were performed on a thermocycler (MJ Research Inc.) using recombinant Pfu DNA polymerase (Stratagene) in a 100-μl reaction volume. The reaction buffer contained 20 mM Tris-HCl (pH 8.2), 10 mM KCl, 6 mM $(NH_4)_2SO_4$, 2 mM $MgCl_2$, 0.1% Triton X-100, 10 μg/ml nuclease-free BSA and 50 μM of each deoxyribonucleoside triphosphate. PCR conditions were 25 cycles of 94° C. for 1 min, 55° C. for 1 min and 72° C. for 2 min, with a final extension step at 72° C. for 7 min.

Figure 1:
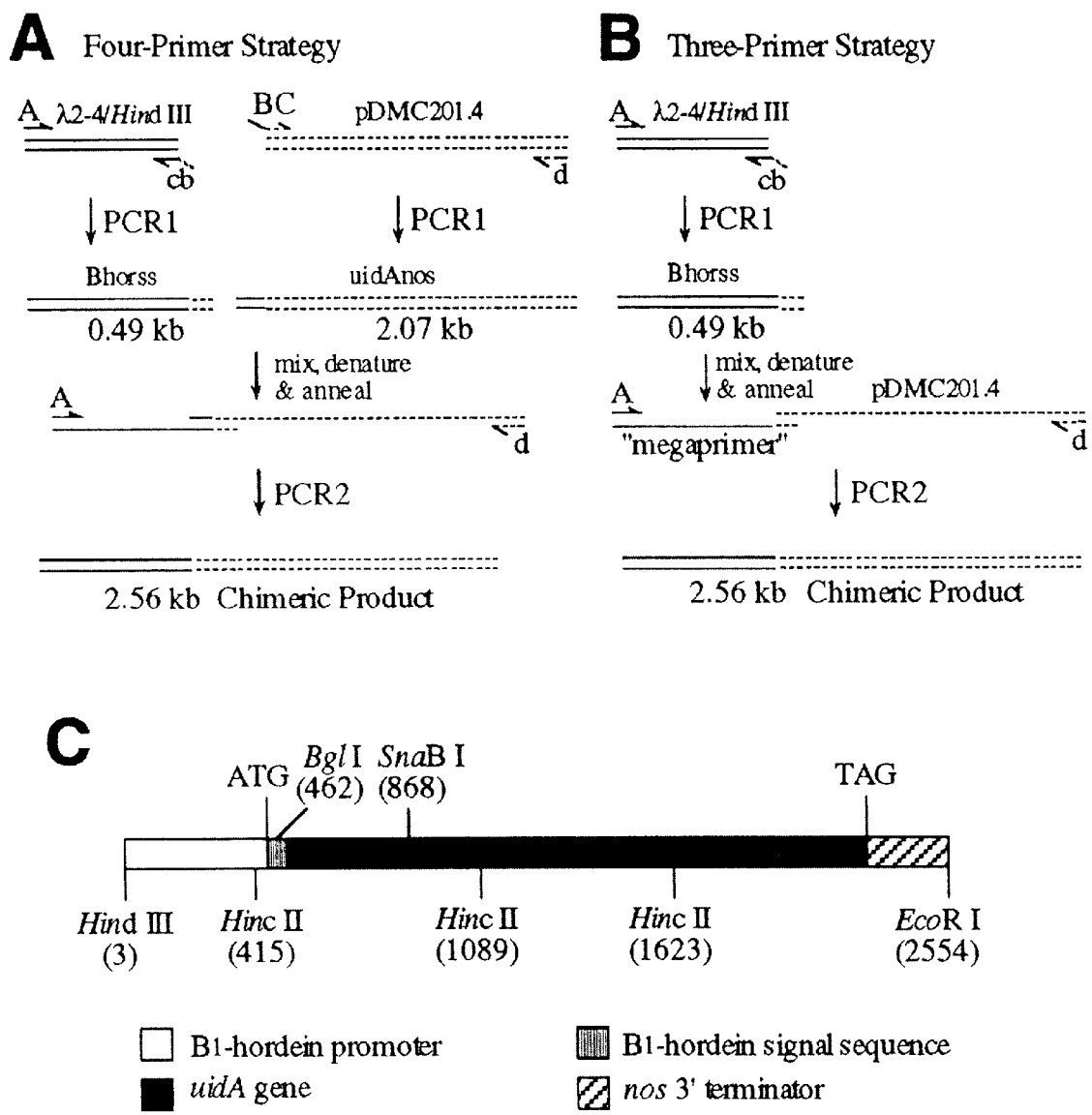
FIG. 1A is a schematic diagram of a four-primer strategy for producing chimeric products using the polymerase chain reaction (PCR).
FIG. 1B is a schematic diagram of a three-primer strategy for producing chimeric products using the polymerase chain reaction (PCR).
FIG. 1C is a map of a construct that includes (from 5' to 3'), the $B_1$-hordein promoter, the $B_1$-hordein signal sequence, the uidA gene, and the nos 3' terminator.

The recombinant PCR strategies are shown in FIG. 1. The two overlapping primers were 5'-GCGGCAACAAGTAC ATTGCATTACGTCCTGTAGAAACCCCA-3' (BC primer) (Seq. I.D. No. 5) and 5'-TGGGGTTTCTACAGGACGTAATGCAAT CGTACTTGTTGCCGC-3' (cb primer) (Seq. I.D. No. 6); the sequence of the cb primer is the reverse complement of the BC primer. These primers contain part of the uidA coding sequence and part of the signal peptide coding sequence from the $B_1$-hordein promoter. The two external primers were 5' GTA<u>AAGCTT</u>TAACAACCCACACA TTG-3' (A primer) (Seq. I.D. No. 7) and 5'-CG <u>GAATTC</u>GATCTAGTA ACATAGAT GACA-3' (d primer) (Seq. I.D. No. 8), each with a unique restriction enzyme site (underlined), Hind III and EcoR I, respectively.

Bhorss ($B_1$-hordein promoter containing the signal peptide sequence) and uidAnos (uidA coding sequence plus nos 3' terminator) fragments were obtained using the following PCR conditions. (I) For Bhorss, 20 ng of template (the □2-4/Hind III plasmid-containing genomic clone of $B_1$ hordein Brandt, et al., 1985) and 40 pmol of primers A and cb were mixed in 100 μl of 1×PCR buffer (Stratagene). (II) For uidAnos, 20 ng of template (the pDMC201.4 plasmid containing promoterless uidA and nos (McElroy et al., 1995); the uidA gene was derived from the pGUSN358->S plasmid modified by site-directed mutagenesis for vacuolar targeting studies (Farrell et al., 1990) and 40 pmol of primers BC and d were mixed in 100 μl of 1×PCR buffer. After addition of 2.5 units of Pfu DNA polymerase, the reaction mixtures were overlaid with 50 μl of mineral oil.

In the four-primer strategy, the two major PCR products in the first reaction were 0.49 kb for Bhorss and 2.07 kb for uidAnos. An aliquot of the first two sets of PCR reactions was diluted 50 times without gel purification and 5 μl of diluted products were directly used as templates for the second PCR reaction. Forty pmol of external primers (A and d primers) and 2.5 units of Pfu DNA polymerase were added to 100 μl of 1×PCR buffer. For the three-primer strategy, a shorter fragment of 0.49 kb Bhorss was produced by PCR in the first reaction and this first PCR product (termed megaprimer) was diluted 50 times. For the second PCR reaction, five μl of the diluted Bhorss megaprimer (Bhorss), twenty ng of template (pDMC201.4) and 40 pmol of external primers (A and d) were mixed to a final volume of 100 μl in 1×PCR buffer.

The second set of PCR reactions using both the modified three- and four-primer strategies produced a 2.56 kb fragment containing the Bhorss and uidAnos DNA fragments (FIG. 1C). A smaller amount of the chimeric product was produced using the 3-primer strategy relative to the 4-primer strategy. A third PCR reaction was carried out to obtain sufficient amounts of the chimeric product for microprojectile bombardment. The PCR product from the 3-primer strategy was diluted 50-fold; 5 μl of this diluted product were added as template to 40 pmol of A/d primers in 100 μl of 1×PCR buffer. The final chimeric products, amplified in a final volume of 2×100 μl (2 reactions) from both 3-primer and 4-primer strategies were purified from a 0.7% agarose gel using QIAquick" gel extraction kit (Qiagen Inc.). The purified DNA fragments were eluted in 50 μl 1×TE buffer, analyzed by restriction enzyme digestion and used in microprojectile bombardment experiments without further subcloning to test DNA construction strategies.

Example 2

Transient Assays in Barley Cells

Prior to microprojectile bombardment, spikes of barley (spring cultivar Golden Promise) containing immature embryos (15–25 days post-pollination) were sterilized in 20% (v/v) bleach (5.25% sodium hypochlorite) for 10–15 min, rinsed briefly 3×5 minutes with sterile water. Endosperm was aseptically separated from each embryo manually and placed "groove-side down" on MS (Murashige and Skoog) basal medium (8) supplemented with 30 mg/l maltose, 1.0 mg/l thiamine-HCl, 0.25 mg/l myo-inositol, 1.0 g/l casein hydrolysate, 0.69 mg/l proline, and solidified with 3.5 g/l Phytagel" (Sigma). DNA bombardment was performed using 1 μm gold particles (Analytical Scientific, Inc.) coated with 12.5 μl of the eluted DNA fragments (approximately 1–2 μg) using the following modifications of a published procedure (Lemaux et al., 1996). Gold particles and other components necessary for precipitation were reduced to half-volume. The DNA/microprojectile precipitate was resuspended in 36 μl of absolute ethanol; 15 μl of the suspension was used per bombardment in a Biolistic PDS-1000/He device (Bio-Rad) at 1100 psi. The bombarded endosperm tissue was incubated at 24±1° C. in the dark for 1 day and stained for GUS activity (Jefferson et al., 1987). The results (not shown) showed expression of GUS in the endosperm tissue and are consistent with the fact that the chimeric DNA construct produced by the PCR reactions described above is in frame thereby allowing production of a functional uidA gene product. Following the in vivo confirmation of functionality, the chimeric product was subcloned into a vector, further confirmed by DNA sequencing and used for stable transformation of barley in order to study protein targeting.

Example 3

Stable Expression of Ph-X Constructs in barley

Materials and Methods

Plants

The two-rowed spring cultivar of barley, Golden Promise, was grown in growth chambers as described previously (Wan and Lemaux 1994; Lemaux et al. 1996).

Nucleic Acids

Plasmid p16 (Sorensen et al. 1996) contains a pUC 18 backbone with the β-glucuronidase gene (uidA; gus) controlled by 550 bp of the barley endosperm-specific $B_1$-hordein promoter and terminated by *Agrobacterium tumefaciens* nopaline synthase 3' polyadenylation signal, nos. Plasmid pD11-Hor3 (Sorensen et al. 1996) contains uidA controlled by 434 bp of the D-hordein promoter and a nos terminator. pAHC20 (Christensen and Quail 1996) contains bar driven by the maize ubiquitin promoter, first intron and terminated by the nos 3'-end. Both of these construct include hordein promoters but do not include a hordein signal sequence. Thus, they are constructs of the type: Ph-X. pAHC25 (Christensen and Quail 1996) consists of uidA and bar, each under the control of the maize ubiquitin (Ubi1) promoter and first intron and terminated by nos.

Transformation Methods

Stable transgenic lines of barley containing $B_1$-hordein-uidA and D-hordein-uidA were obtained following modifications of a published protocol (Wan and Lemaux 1994; Lemaux et al. 1996). The modifications were required for transformation of commercial genotypes of barley, and the method described herein may be used to transform commercial genotypes of monocots including barley and wheat that are recalcitrant to transformation using published methods (for example, the barley genotypes Harrington, Morex, Crystal, Stander, Moravian III, Galena, Salome, Steptoe, Klages and Baronesse and the wheat genotypes Anza, Karl, Bobwhite and Yecora Rojo).

Donor barley plants for immature embryos were grown in soil under controlled conditions in growth chambers as described (Wan and Lemaux, 1994; Lemaux et al., 1996). Immature zygotic embryos were surface-sterilized, placed scutellum-side down on DBC2 medium, and incubated at 24±1° C. Regenerative tissues were maintained for 3–4 weeks, then cut into small pieces (about 3 to 5 mm), transferred to fresh DBC2 medium, and grown under dim light conditions. After an additional three weeks, green callusing sectors were broken into pieces (about 3 to 5 mm) and transferred to fresh DBC2 medium. Green regenerative tissues were maintained on DBC2 medium with subculturing at 3- to 4-week intervals.

For bombardment, green regenerative tissues (about 3 to 5 mm, four-months old) were placed in the dark at 24±1° C. for one day, then transferred to DBC2 medium containing 0.2 M mannitol and 0.2 M sorbitol. Four hours after treatment with the osmoticum, green tissues were bombarded as described by Lemaux et al. (1996) with gold particles (Analytical Scientific Instruments, Alameda, Calif.) coated with pAHC25, a mixture of pAHC20 and p16 (1:2 molar ratio), or a mixture of pAHC20 and pD11-Hor3 (1:2 molar ratio). At 16–18 hours after bombardment, the green tissues were transferred to DBC2 medium without osmoticum and grown at 24±1° C. under dim light conditions (about 10 $\mu$E, 16 h-light).

Following an initial 3- to 4-week culturing period on nonselective medium, each piece of green tissue was broken into 1 to 2 pieces (about 4 mm to 5 mm, depending on size of original tissue piece) and transferred to DBC2 medium supplemented with 5 mg/L bialaphos for bar selection. Green tissues were selected on DBC2 medium and 4 mm to 5 mm tissues subcultured at 3- to 4-week intervals. Bialaphos-resistant calli were regenerated on FHG (Hunter 1988) medium containing 1 mg/L 6-benzylaminopurine (BAP) and 3 mg/L bialaphos. Regenerated shoots were transferred to Magenta boxes containing rooting medium (callus-induction medium without phytohormones) containing 3 mg/L bialaphos. When shoots reached the top of the box, plantlets were transferred to soil and grown to maturity in the greenhouse.

The DBC2 medium used for transformation is based on MS medium (Murashige and Skoog, 1962) supplemented with 30 g/L maltose, 1.0 mg/L thiamine-HCl, 0.25 g/L myo-inositol, 1.0 g/L casein hydrolysate, 0.69 g/L proline, and solidified with 3.5 g/L Phytagel (Sigma, St. Louis, Mo.). The medium was further supplemented with 2.5 mg/L of the plant auxin 2,4-dichlorophenoxyacetic acid (2,4-D), 0.1 mg/L of the plant cytokinin 6-benzylamino purine (BAP) and 5 $\mu$M copper (as copper sulfate). The presence of elevated copper and the high auxin/low cytokinin ratio were found to be required for efficient generation of the green regenerative material from genotypes of barley and wheat that are otherwise recalcitrant to transformation. However, the composition of the DBC2 medium can be varied depending on the particular genotype that is to be transformed. The key ingredients of the medium will be within the following ranges: an auxin at a concentration of about 0.1 mg/L to about 5 mg/L, a cytokinin at a concentration of 0 mg/L to about 5 mg/L and copper at a concentration of about 0.1 $\mu$M to about 50 $\mu$M (and more typically about 1 to 10 $\mu$M). More efficient transformation may be obtained when maltose is employed as a carbon source in the medium at a concentration of up to about 60 g/L, more typically about 30 g/L (either in place of or in combination with sucrose).

Histochemical staining for GUS was performed (Jefferson et al. 1987) using 5-bromo-4-chloro-3-indoxyl-$\beta$-D-glucuronic acid (X-gluc) (Gold Biotechnology, Inc., St. Louis, Mo.). Samples were incubated overnight at 37° C. in GUS assay buffer.

Quantitative GUS activity measurements were performed by the method of Jefferson et al. (1987) using 4-methylumbelliferyl-$\beta$-D-glucuronide (MUG) substrate (Sigma, St. Louis, Mo.). From homozygous lines a single immature endosperm was isolated at 10–14, 20 and 30 days after pollination or from mature endosperm, frozen in liquid nitrogen, and ground in GUS extraction buffer; each treatment had 4 replicates. After centrifugation the supernatants were used to determine GUS activity. Fluorescence of 4-methylumbelliferone (4-MU) (Sigma, St. Louis, Mo.) was measured on a TKO 100 dedicated mini fluorometer (Hoefer Scientific Instruments, San Francisco, Calif.) at an excitation wavelength of 365 nm and an emission wavelength of 460 nm. Proteins were extracted as described previously (Jefferson 1987; Jefferson et al. 1987) and protein concentrations in extracts were measured according to Bradford (1976) using Bio-Rad reagent (Bio-Rad, Richmond, Calif.).

To determine herbicide sensitivity of $T_0$ plants and their progeny, a section of leaf blade at the 4- to 5-leaf stage was painted using a cotton swab with a 0.25% solution (v/v) of Basta™ solution (starting concentration, 200 g/L phophinothricin, Hoechst AG, Frankfurt, Germany) plus 0.1% Tween 20. Plants were scored 1 week after herbicide application.

Total genomic DNA from independent calli or leaf tissues was purified as described by Dellaporta (1993). To test for the presence of uidA in genomic DNA of putatively transformed lines, 250 ng of genomic DNA was amplified by PCR using the primer set, UIDA1 (5'-AGCGGCCGCATTACGTCCTGTAGAAACC-3') (Seq. I.D. No. 9) and UID2R (5'-AGAGCTCTCATTGTTTGCCTCCC TG-3') (Seq. I.D. No. 10). The presence of bar was tested using the primer set, BAR5F (5'-CATCGAGACAAGCACGGTCAACTTC-3') (Seq. I.D. No. 11) and BAR1R (5'-ATATCCGAGCGCC TCGTGCATGCG-3') (Seq. I.D. No. 12) (Lemaux et al. 1996). Amplifications were performed with Taq DNA polymerase (Promega, Madison, Wis.) in a 25-$\mu$l reaction. Twenty-five pl of the PCR product with loading dye was electrophoresed on a 0.8% agarose gel with ethidium bromide and photographed using UV light. Presence of a 1.8-kb fragment with UIDA primers was consistent with an intact uidA fragment; an internal 0.34-kb fragment was produced with BAR primers. For DNA hybridization analysis, 10 $\mu$g of total genomic DNA from leaf tissue of each line was digested with EcoRI and BamHI, separated on a 1.0% agarose gel, transferred to Zeta-Probe GT membrane (Bio-Rad, Hercules, Calif.) and hybridized with a radiolabeled uidA-specific probe following the manufacturer's instructions. The uidA-containing 1.8 kb XbaI-fragment from pBI221 was purified using a QIAEX gel extraction kit (QIAGEN, Chatsworth, Calif.) and labeled with $\alpha$-$^{32}$P-dCTP using random primers.

Results

Twenty-two independent stably transformed barley callus lines containing either $B_1$- or D-hordein promoter-uidA fusions were obtained in a first series of transformations. Thirteen lines were regenerable, seven $B_1$-hordein-uidA transformants and six D-hordein-uidA transformants. Genomic DNA from the callus of regenerable transformants was isolated. PCR analysis was performed using UIDA and BAR primers. PCR amplification resulted in a 1.8-kb intact uidA and a 0.34-kb internal bar fragment in $T_1$ progeny. From $T_0$ leaf tissue of the 13 lines tested, however, one (GPDhGN-22) did not produce a PCR-amplified fragment for uidA (Table 2). Following Southern hybridization of genomic DNA from leaf tissue of the 7 $B_1$- hordein-uidA and 6 D-hordein-uidA transformants, twelve of the thirteen transformed lines produced the expected 2.35-kb or 2.25-kb hordein-uidA fusion fragments. The remaining line (GPDhGN-22) did not produce any uidA-hybridizing fragments, although this line contained the appropriated-sized bar-hybridizing bands (data not shown).

Different tissues from stable transformants were tested for histochemical GUS activity. Strong GUS expression was seen in endosperm tissues transformed with both $B_1$- and D-hordein promoters, but not in embryo, ovary, stigma, anther or leaf tissues. GUS expression under control of the maize ubiquitin (Ubi1) promoter was observed in all tissues: no GUS expression was observed in the nontransformed control. Germinating roots and shoots from $T_1$ seed of either $B_1$- or D-hordein promoter-uidA fusion transformants also did not have observable histochemical GUS activity (data not shown).

Relative activities of the $B_1$- and D-hordein-uidA constructs were determined by fluorometric analysis of GUS in extracts of developing and mature seeds of homozygous lines (Table 1). The specific acitivities of GUS driven by the $B_1$-promoter-driven GUS had maximum levels expression at 10 to 20 days post-pollination. The D-hordein promoter showed a developmental pattern with peak specific activities at 20 to 30 days post-pollination.

Enzyme actvity of phosphinothricin acetyltransferase (PAT, product of bar) and GUS in $T_1$ plants and their progeny was tested by painting leaves with Basta for PAT and by histochemical assay for GUS. Leaf tissue from $T_0$ plants of all thirteen independent lines exhibited Basta-resistance (Table 2). In $T_1$ progeny seven out of the thirteen lines tested for both uidA and bar showed a 3:1 segregation pattern for expression of GUS (Table 2). Of the remaining six lines, one line (GPDhGN-6) had a 43:2 segregation ratio for GUS expression; one line (GPDhGN-22) expressed PAT but did not contain uidA, one line (GPBhGN-13) did not contain both uidA and bar, and three lines (GPBhGN-2, GPDhGN-12 and GPDhGN-14) were sterile. $T_1$ endosperm from all fertile $T_0$ transgenic lines having positive DNA hybridization signals for uidA [2.35-kb and 2.25-kb fragments for the $B_1$-hordein-uidA and D-hordein-uidA genes, respectively], exhibited strong GUS activity (Table 2) except GPBhGN-13 and GPDhGN-14. The bar gene was stably transmitted to $T_1$ progeny of all fertile lines except GPBhGN-13; one stably expressing homozygous line (GPDhGN-16) was obtained (Table 2). Expression of uidA driven by either the $B_1$- or D-hordein promoter was also stably inherited in $T_2$ progeny of all 7 independent lines tested (GPBhGN-4, -7, -12, -14, GPDhGN-6, -11 and 16) (Table 1). Expression of the uidA gene was stably transmitted in the one line tested at the $T_5$ generation (GPBhGN-4), in the two lines tested at $T_4$ (GPBhGN-7 and GPDhGN-16), 3 lines at $T_3$ (GPBhGN-12, GPDhGN-6 and -11), 1 line at $T_2$ (GPBhGN-14) and 1 line at $T_1$ (GPBhGN-3) (Table 1). Homozygous transgenic lines stably expressing uidA were obtained from events GPBhGN-4, -7, GPDhGN-6 and -16 (Tables 1 and 2).

TABLE 1

Analysis of $T_0$ barley plants and their progeny transformed with $B_1$— and D-hordein-uidA fusions

| Plasmids used for bombardment | Transgenic barley lines | $T_0$ bar | uidA (PCR) | $T_1$ uidA (+/−) | $T_1$ bar (+/−) | $T_2$ uidA (+/−) | $T_2$ bar (+/−) | $T_3$ uidA (+/−) | $T_3$ bar (+/−) | $T_4$ uidA (+/−) | $T_4$ bar (+/−) | $T_5$ uidA (+/−) | $T_5$ bar (+/−) |
|---|---|---|---|---|---|---|---|---|---|---|---|---|---|
| p16 + pAHC20 | B2 (GPBhGN-2)*a | + | + | | | | | | | | | | |
| | B3 (GPBhGN-3) | + | + | 11/3 | | | | | | | | | |
| | B4 (GPBhGN-4) | + | + | 70/20 | 25/10 | | | | | | | | |
| | B4-34 | | | | | 17:0 | 0/14 | | | | | | |
| | B4-34-6-3 | | | | | | | | | 41/0 | | | |
| | B4-34-6-4 | | | | | | | | | 51/0 | | | |
| | B4-34-6-5 | | | | | | | | | 39/0 | | | |
| | B4-34-6-6 | | | | | | | | | 35/0 | | | |
| | B4-34-7 | | | | | | | 48/0 | 0/9 | | | | |
| | B4-34-7-1 | | | | | | | | | 38/0 | 0/8 | | |
| | B4-34-7-2 | | | | | | | | | 26/0 | | | |
| | B4-34-7-3 | | | | | | | | | 23/0 | | | |
| | B4-34-7-4 | | | | | | | | | 25/0 | | | |
| | B4-34-7-1-1 | | | | | | | | | | | 22/0 | |
| | B4-34-7-1-2 | | | | | | | | | | | 73/0 | |
| | B7 (GPBhGN-7) | + | + | 45/18 | 18/6 | | | | | | | | |
| | B7-2 | | | | | 25/0 | 13/1 | | | | | | |
| | B7-2-1 | | | | | | | 32/0 | 14/4 | | | | |
| | B7-2-1-1 | | | | | | | | | 20/0 | | | |
| | B7-2-1-2 | | | | | | | | | 59/0 | | | |
| | B7-2-1-3 | | | | | | | | | 38/0 | | | |
| | B7-2-2-4 | | | | | | | | | 24/0 | | | |
| | B7-2-2 | | | | | | | n.t. | 6/7 | | | | |
| | B12(GPBhGN-12)** | + | + | 21/12 | 15/2 | | | | | | | | |
| | B12-2 | | | | | 9/11 | 5/2 | | | | | | |
| | B12-2-2 | | | | | | | 4/9 | | | | | |
| | B12-2-3 | | | | | | | 1/2 | | | | | |
| | B12-4 | | | | | 2/0 | 6/4 | | | | | | |
| | B13 (GPBhGN-13)** | + | + | 0/21 | 0/46 | | | | | | | | |
| | B13-1 | | | | | 0/26 | 2/14 | | | | | | |
| | B13-1-8 | | | | | | | 0/20 | | | | | |
| | B13-1-12 | | | | | | | 0/27 | | | | | |
| | B13-2 | | | | | 0/17 | 0/15 | | | | | | |
| | B14 (GPBhGN- | + | + | 19/12 | 20/9 | | | | | | | | |

TABLE 1-continued

Analysis of T₀ barley plants and their progeny transformed with B₁— and D-hordein-uidA fusions

| Plasmids used for bombardment | Transgenic barley lines | T₀ bar | T₁ uidA (PCR) | T₁ uidA (+/−) | T₁ bar (+/−) | T₂ uidA (+/−) | T₂ bar (+/−) | T₃ uidA (+/−) | T₃ bar (+/−) | T₄ uidA (+/−) | T₄ bar (+/−) | T₅ uidA (+/−) | T₅ bar (+/−) |
|---|---|---|---|---|---|---|---|---|---|---|---|---|---|
| pD11-Hor3 + pAHC20 | 14)** B14-1 | | | | | 10/1 | 11/1 | | | | | | |
| | D6 (GPDhGN-6)** | + | + | 43/2 | 8/7 | | | | | | | | |
| | D6-3 | | | | | 40:1 | 2/10 | | | | | | |
| | D6-3-3 | | | | | | | 18/1 | | | | | |
| | D6-3-4 | | | | | | | 51:0 | | | | | |
| | D6-3-5 | | | | | | | 60:1 | | | | | |
| | D6-9 | | | | | 24:1 | 1/7 | | | | | | |
| | D6-9-1 | | | | | | | 24/0 | | | | | |
| | D6-9-6 | | | | | | | 81:0 | | | | | |
| | D6-9-7 | | | | | | | 39/1 | | | | | |
| | D11 (GPDhGN-11)** | + | + | 17/10 | 2/1 | | | | | | | | |
| | D11-2 | | | | | 1/0 | 9/1 | | | | | | |
| | D11-2-3 | | | | | | | 2/1 | | | | | |
| | D12 (GPDhGN-12)*ᵃ | + | + | | | | | | | | | | |
| | D14 (GPDhGN-14)*ᵇ | + | + | n.t.ᶜ | 1/2 | | | | | | | | |
| | D14-1 | | | | | 0/20 | 12/5 | | | | | | |
| | D14-1-9 | | | | | | | 0/28 | | | | | |
| | D14-1-10 | | | | | | | 0/29 | | | | | |
| | D14-1-13 | | | | | | | 0/25 | | | | | |
| | D14-1-15 | | | | | | | 0/14 | | | | | |
| | D16 (GPDhGN-16)** | + | + | 7/2 | 7/1 | | | | | | | | |
| | D16-5 | | | | | 25/18 | 4/0 | | | | | | |
| | D16-5-2 | | | | | | | 4/0 | 15/0 | | | | |
| | D16-5-2-3 | | | | | | | | | 19/0 | | | |
| | D16-5-2-7 | | | | | | | | | 9/0 | | | |
| | D16-5-2-8 | | | | | | | | | 10/0 | | | |
| | D16-5-2-10 | | | | | | | | | 5/0 | | | |
| | D22 (GPDhGN-22)*ᵃ | + | − | | | | | | | | | | |

Expression of bar and uidA was tested by Basta painting and histochemical GUS assay, respectively, except for confirmation of uidA in T₀ plants by PCR
*Sterile
**Tetraploid
ᵃChromosomes were not counted
ᵇOutcrossed with nontransgenic plants
ᶜn.t. not tested

TABLE 2

Specific GUS activities in developing and mature transgenic barley seeds

| Days after pollination | GUS activity (pmol/min/mg protein) | | | |
|---|---|---|---|---|
| Transgenic line | 10–14 | 20 | 30 | mature |
| GPBhGN-4-34-7-1-2 | 3514 ± 1326 | 2309 ± 454 | 1313 ± 340 | 106 ± 37 |
| GPDhGN-6-9-6 | 402 ± 363 | 3812 ± 969 | 2806 ± 949 | 281 ± 52 |
| Nontransgenic control | 80 ± 31 | 81 ± 23 | 36 ± 13 | 43 ± 9 |

GUS activity was determined by the fluorometric assays of protein extracts from developing and mature endosperm of homozygous lines. Values for GUS activity represent mean ± standard deviation of four replicates for each treatment
GPBhGN-4-34-7-1-2 and GPDhGN-6-9-6 are homozygous lines transformed with B₁-hordein-uidA (p16) and D-hordein-uidA (pD11-Her3) constructs, respectively, producing T₅ and T₃ seeds, respectively Example 4

Figure 2:
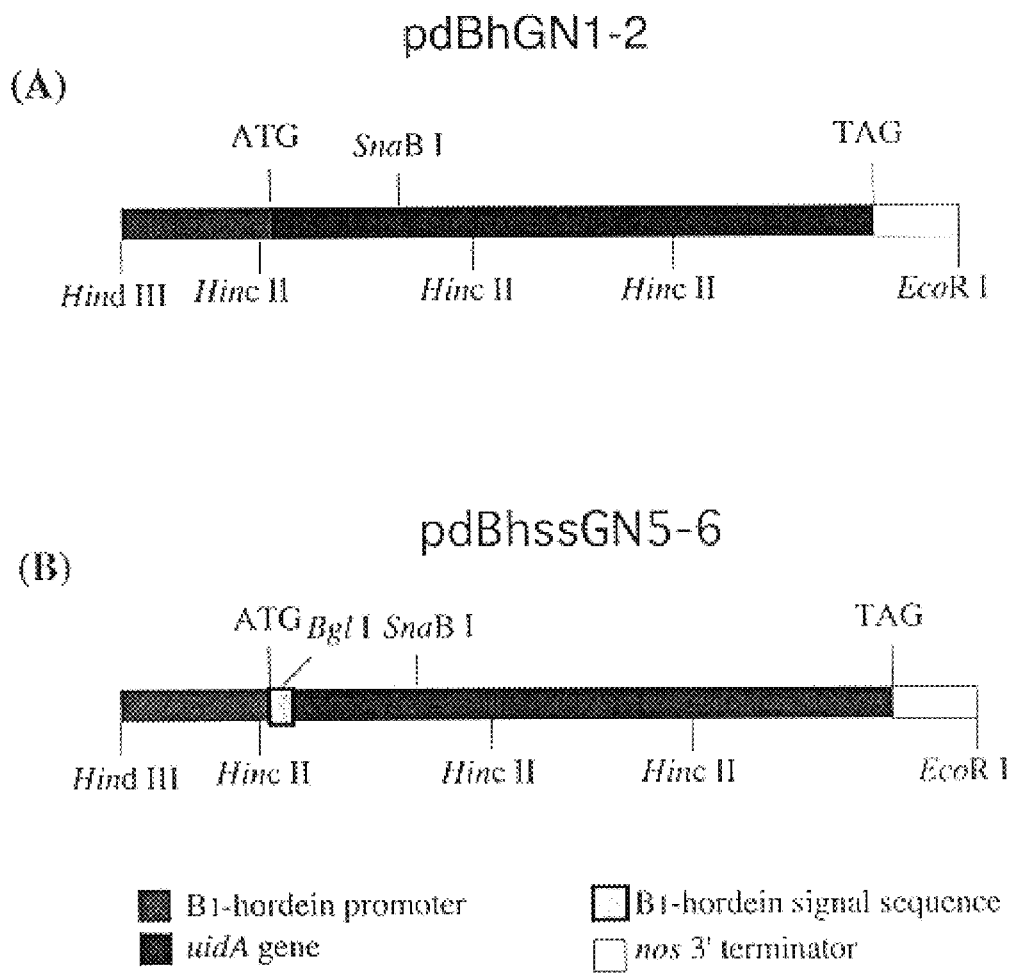
FIGS. 2A and B show alignments of constructs comprising the $B_1$-hordein promoter, the uidA gene, and the nos 3' terminator, with (2B) or without (2A) the $B_1$-hordein signal sequence.

Comparison of Seed Expression in Barley Plants Stably Transformed with Ph-hSS-X or Ph-X Constructs To ascertain the effect of the hordein signal sequence on protein expression levels, barley plants were transformed with constructs in which the hordein B₁ promoter was operably linked to the uidA gene either with the hordein B₁ signal sequence (construct pdBhssGN5-6) or without the signal sequence (construct pdBhGN1-2) as illustrated in FIG. 2. Details and results of these procedures are described below.

Materials and Methods

Plasmids

Two DNA constructs containing the $B_1$-hordein promoter and gus coding region with or without the signal peptide sequence were made to test the functionality of the $B_1$-hordein promoter-gus fusions and to study its targeting:

(1) pdBhssGN5-6 (with signal sequence, FIG. 2A): the chimeric DNA construct containing the $B_1$-hordein promoter-signal sequence-uidA-nos, produced using the PCR methods described in Example 1, was digested with HindIII and SnaBI, and the HindIII/SnaBI fragment was ligated into HindIII/SnaBI-digested pDMC201.4 (McElroy et al., 1995) to generate the pdBhssGN5-6 plasmid. The pDMC201.4 plasmid contains promoterless uidA and nos; the uidA gene was derived from the pGUSN358->S plasmid modified by site-directed mutagenesis for vacuolar targeting studies (Farrell and Beachy, 1990). The PCR-amplified fragment ($B_1$-hordein promoter with its signal peptide sequence plus the junction region with the 5' uidA) of the chimeric product was confirmed by DNA sequencing.

(2) pdBhGN1-2 (without signal sequence, FIG. 2B): primers Bhor3 (5'-cgcatgcGTGCAGGTGTATGAGTCATT-3') (Seq. I.D. No. 13) and Bhor2R (5'-ccctctagaAGTGGATTGGTGTTAACT-3') (Seq. I.D. No. 14) containing SphI and XbaI sites, each with a unique restriction enzyme site (small letters), respectively, were used for amplification of 0.55-kb $B_1$-hordein 5' region using the pl6 plasmid containing $B_1$-hordein promoter-uidA-nos (Sørensen et al., 1996) as a template. The 0.55-kb PCR-amplified fragment was digested with SphI and XbaI and ligated into SphI/XbaI-digested pUC19 to generate pBhor-1. pBhGN-1 was made by replacing CaMV35S promoter in p35SGN-3 (containing CaMV35S promoter-uidA-nos) with the SphI/XbaI $B_1$-hordein fragment from pBhor-1. The HindIII/SnaBI fragment from pBhGN-1 was replaced with the HindIII/SnaBI fragment in pDMC201.4 to generate pdBhGN1-2. Thus, the 120-bp 5' $B_1$-hordein flanking region was deleted in both pdBhssGN5-6 and pdBhGN1-2.

The resulting two chimeric DNA constructs were introduced using microprojectile bombardment into immature barley endosperm tissues for stable gene expression assays. Stable transformation methods, GUS staining and quantitation, and Basta sensitivity were determined as described in Example 3.

Genomic DNA isolation, polymerase chain reaction (PCR) and DNA blot hybridization Total genomic DNA from independent calli or leaf tissues was purified as described (Dellaporta, 1993). To test for the presence of uidA in genomic DNA of putatively transformed lines, 250 ng of genomic DNA was amplified by PCR using the primer set, UIDA1 and UID2R. The primer set, Bhor8 (5'-GAAGAGATGAAGCCTGGCTAC-3') (Seq. I.D. No. 15) and GUS5516 (5'-CGATCCAGACTGAATGCC CACAGG-3') (Seq. I.D. No. 16) was used to distinguish between the $B_1$-hordein promoter with and without the signal sequence. A 229-bp hybrid product is expected from the construct containing the $B_1$-hordein promoter with the signal sequence while a 178-bp PCR product is expected from the construct containing the $B_1$-hordein promoter without the signal sequence. The presence of bar was tested using the primer set, BAR5F and BAR1R (Lemaux et al. 1996). Amplifications were performed with Taq DNA polymerase (Promega, Madison, Wis.) in a 25-$\mu$l reaction. Twenty-five $\mu$l of the PCR product with loading dye was electrophoresed on a 0.8% agarose gel with ethidium bromide and photographed using UV light. Presence of a 1.8-kb fragment with UIDA primers was consistent with an intact uidA fragment; an internal 0.34-kb fragment was produced with BAR primers. For DNA hybridization analysis, 10 $\mu$g of total genomic DNA from leaf tissue of each line was digested with HindII and SacI, separated on a 1.0% agarose gel, transferred to Zeta-Probe GT membrane (Bio-Rad, Hercules, Calif.) and hybridized with a radiolabeled uidA-specific probe following manufacturer's instructions. The uidA-containing 1.8 kb XbaI-fragment from pBI221 was purified using a QIAEX gel extraction kit (QIAGEN, Chatsworth, Calif.) and labeled with $\alpha$-$^{32}$P-dCTP using random primers.

Immunogold labeling assay

Transgenic and nontransgenic immature endosperm were harvested about 20 days after pollination using a high pressure freezing method (McDonald, 1998). The tissues were embedded in white resin and immunocytochemistry was performed as previously described (Phillip et al., 1998)

Results

PCR and DNA blot hybridization analysis of transgenic plants

To test the functionality of the N-terminal signal peptide sequence of the $B_1$-hordein promoter and to study targeting mechanisms, we obtained 10 independent stably transformed barley lines containing either pdBhssGN5-6 or pdBhGN1-2. Of these, three lines from each DNA construct were co-expressed lines with uidA and bar genes. Genomic DNA from these transformants was isolated. PCR analysis was performed using UIDA and BAR primers. PCR amplification resulted in 1.8-kb intact uidA and 0.34-kb internal bar fragments from all six lines (Table 3). A 51 bp size difference between the fragments amplified from the $B_1$-hordein-uidA transformants with and without the signal sequence was observed and is accounted for by the presence of the signal sequence in lines GPdBhGN-1, -2 and -16.

Hordein-uidA expression in trangenic plants $T_1$ seeds were tested for histochemical GUS activity. Strong GUS expression was seen in endosperm tissues transformed with both $B_1$-hordein promoters with and without the signal sequence, but not in the embryo. GUS expression from the two $B_1$-hordein-uidA constructs was very evident in developing endosperm, especially in peripheral cells of endosperm tissue and endosperm tissue near the scutellar side. The $B_1$-hordein promoter with the signal sequence had even stronger expression in endosperm than did that without the signal sequence. No GUS expression was observed in the nontransformed control tissues.

Figure 6:
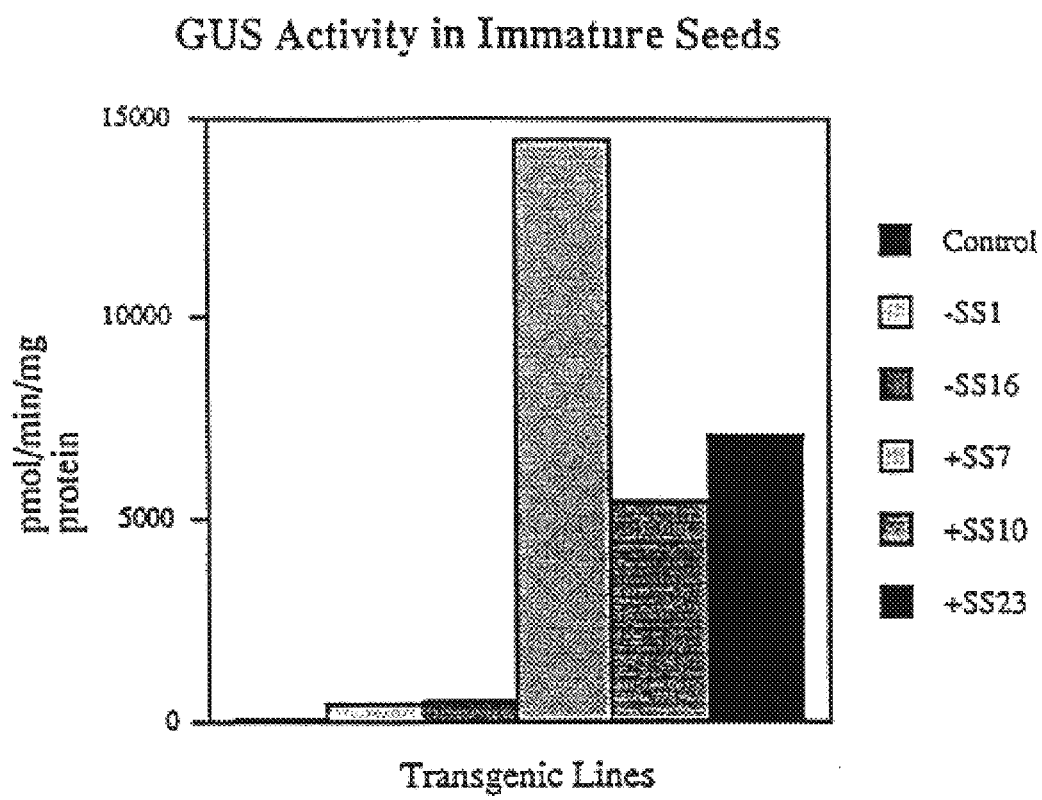
FIG. 6 is a bar graph showing GUS activity in immature barley seeds expressing constructs comprising the $B_1$-hordein promoter, the uidA gene, and the nos 3' terminator either with (+SS) or without (−SS) the $B_1$-hordein signal sequence.
Figure 7:
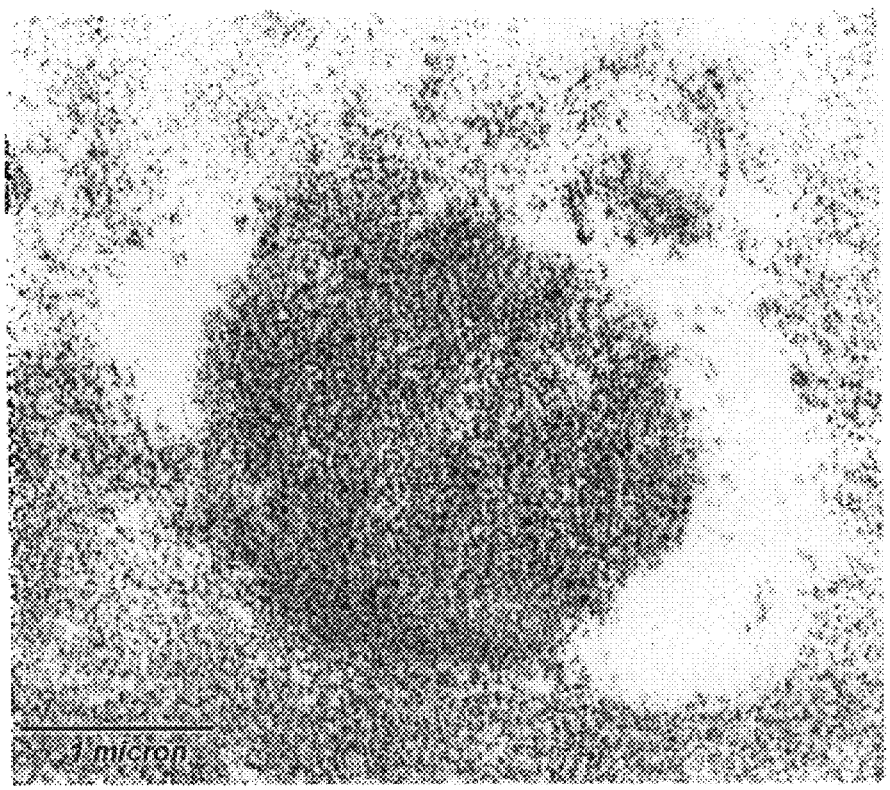
FIG. 7 is an electron photomicrograph in which an immunosignal is specific for protein bodies in GUS-expressing immature endosperm of a line that was transformed with the $B_1$-hordein-uidA DNA construct containing the 19 amino acid N-terminal signal peptide sequence.

Relative activities of the $B_1$-hordein-uidA constructs were determined by fluorometric analysis of GUS in extracts of developing and mature seeds of homozygous lines. The specific activities of GUS driven by the $B_1$-hordein promoter with the signal sequence were higher in both developing and mature seeds than without the signal sequence (FIGS. 6 and 7). In particular, developing endosperm tissues transformed with the $B_1$-hordein promoter with the signal sequence had more than 30 times GUS activity, compared with the $B_1$-hordein promoter without the signal sequence.

Analysis of $T_0$ to $T_2$ progeny

Enzyme activity of phosphinothricin acetyltransferase (PAT, product of bar) and GUS in $T_0$ plants and their progeny was tested by painting leaves with Basta for PAT and by histochemical assay for GUS. Leaf tissue from $T_0$ plants of all six independent lines exhibited Basta resistance (Table 1). In $T_1$ progeny all six lines tested for uidA showed a 3:1 segregation pattern for expression of GUS. The bar gene was also stably transmitted to $T_1$ progeny of five lines except GPdBhssGN-10; the GPdBhssGN-10 line did not expressed PAT. Homozygous transgenic lines stably expressing uidA were obtained from 4 events GPdBhGN-1, GPdBhssGN-7, -10, and -23.

Electron Microscopy and immunogold labeling

The immunosignal seen at the electron microscopic level was specific for protein bodies in GUS-expressing immature endosperm of line that was transformed with the $B_1$-hordein-uidA DNA construct containing the 19 amino acid N-terminal signal peptide sequence (FIG. 7).

Discussion

The foregoing research tested the functionality of the barley $B_1$-hordein promoters with and without the 19 amino acid N-terminal signal peptide sequence using both transient and stable expression assays in barley. Consistent with earlier studies (Müller and Knudsen 1993; Sørensen et al. 1996), transient expression of GUS under the control of the $B_1$-hordein promoter-uidA fusion without the signal sequence was observed in developing endosperm, but not in embryos. The $B_1$-hordein promoter with the signal sequence exhibited the same expression pattern, but with stronger expression. PCR analysis confirmed the presence of uidA and bar in genomic DNA from $T_0$ plants of 6 different lines stably transformed with $B_1$-hordein promoters with and without the signal sequence.

Stably transformed, developing and mature barley seeds were characterized in terms of tissue-specificity and timing of hordein promoter-driven GUS expression. GUS driven by both $B_1$-hordein promoters with and without the signal sequence was expressed exclusively in endosperm tissue, not in other tissues. In addition, the existence of the signal sequence with the $B_1$-hordein promoter dramatically enhanced GUS expression in developing transgenic. endosperm. This is consistent with the results of Fiedler and Conrad (1995) that an antigen-binding single chain Fv (scFv) protein was only detectable in seeds of tobacco plants transformed with constructs containing a signal peptide sequence. After storage of mature transgenic tobacco seeds for one year at room temperature, there was no loss of scFv protein or its antigen-binding activity whereas in plants transformed with a construct without a signal peptide no detectable accumulation of scFv in ripe or developing seeds occurred. They speculated that the lack of GUS protein expression in cytosol is a result of translational or post-translational regulation by cytosolic proteases, which degrade the scFv protein if it does not enter the secretory pathway. In contrast, the levels of GUS mRNAs in developing seeds and GUS activity in mature seeds were consistently higher in transformed tobacco lines that contained the 32 amino acid N-terminal amino acid sequence of soybean embryo-specific lectin gene as compared with those that lacked this sequence (Phillip et al., unpublished observation). GUS expression from the two $B_1$-hordein-uidA constructs was very evident especially in peripheral cells of developing endosperm tissue and endosperm tissue near the scutellar side in transformed barley.

Transgenic plants with a single site of transgene integration would be expected to give a segregation ratio for the transgene (and its expression) of 3:1. All six lines gave such a ratio for GUS expression. Homozygous, stably expressing GUS transgenic lines were obtained from 4 lines. Expression of the maize ubiquitin promoter-driven PAT was also stably inherited in $T_1$ progeny of five transgenic lines; however, one line (GPdBhssGN-10) did not show PAT expression In $T_2$ progeny.

The results presented here show that the D- or $B_1$-hordein promoter can be used to develop a system for limiting foreign gene expression exclusively to the endosperm of barley seed. In addition, the results show that the use of plants transformed with a seed-specific promoter with the signal sequence dramatically enhanced the transgene expression. This permits the creation of new crop varieties for neutraceutical and pharmaceutical purposes using vacuolar targeting strategies.

Example 5

Embryo Specific Expression

This example uses the maize Glb1 promoter, with or without deletion of a 5' flanking sequence, fused to the bacterial reporter gene, β-glucuronidase gene (uidA; gus), to demonstrate the functionality of the maize Glb1 promoter in transgenic barely, for embryo specific expression.

A two-rowed spring cultivar of barley, Golden Promise, was grown in growth chambers as described previously (Wan and Lemaux 1994; Lemaux et al. 1996).

Plasmids ppGlb1GUS (Liu and Kriz, 1996), a plasmid containing uidA reporter gene under the control of the maize embryo-specific globulin (Glb1) promoter and terminated by nos, was obtained from DEKALB Plant Genetics, Mystic, Conn. The ppGlb1GUS was digested with EcoRI to remove a 1.04-kb 5' globulin flanking region. The 2.58-kb EcoRI fragment containing the 0.36-kb globulin promoter, uidA coding sequence and nos 3' terminator was ligated into EcoRI-digested pUC19 to generate pdGlbGUS-6. Thus, the 1.04-kb 5' globulin flanking region was deleted in pdGlbGUS-6. The above two chimeric DNA constructs were introduced using microprojectile bombardment into immature barley endosperm tissues for both transient and stable gene expression assays.

Transient gene expression of the uidA genes driven by globulin-promoters

Spikes about 20 to 25 days after pollination were surface-sterilized for 10 to 15 min in 20% (v/v) bleach (5.25% sodium hypochlorite), followed by 3 washes with sterile water. Immature embryos and endosperm tissues were aseptically separated and placed scutellum-side up on MS medium (Murashige and Skoog 1962) supplemented with 3.5 g/L of Phytagel (Sigma, St. Louis, Mo.) with or without osmoticum treatment (Cho et al., 1998b). The tissues were bombarded using a Biolistic PDS-1000 He gun (Bio-Rad, Hercules, Calif.) at 1100 psi with 1.0 μm gold particles coated with either ppGlb1GUS or pdGlbGUS-6 according to the protocol of Lemaux et al. (1996). Osmotic treatment includes 0.2 M mannitol and 0.2 M sorbitol to give a final concentration of 0.4 M with 4-h pre-treatment and 1- or 2-d post-treatment.

Stable barley transformations

Stable transgenic GP lines were obtained via microparticle bombardment essentially as described in Wan and Lemaux 1994; Lemaux et al. 1996; and Cho et al., 1998a. Gold particles (1.0 μm) were coated with 25 μg of 1:1 molar ratio of pAHC20 and ppGlb1GUS or pdGlbGUS-6, and used in bombardment experiments as described above. Plasmid pAHC20 (Christensen and Quail, 1996) contains the herbicide resistance gene, bar, from *Streptomyces hygroscopicus* under the control of the maize ubiquitin Ubi1 promoter and first intron and nos 3' terminator. Bialaphos-resistant calli were regenerated on FHG (Hunter 1988) medium containing 1 mg/L 6-benzylaminopurine (BAP) and 3 mg/L bialaphos. Regenerated shoots were transferred to Magenta boxes containing rooting medium (callus-induction medium without phytohormones) containing 3 mg/L bialaphos. When shoots reached the top of the box, plantlets were transferred to soil and grown to maturity in the greenhouse.

Histochemical and quantitative assays of GUS activity

Histochemical staining for GUS was performed using 5-bromo-4-chloro-3-indoxyl-β-D-glucuronic acid (X-gluc) (Gold Biotechnology, Inc., St. Louis, Mo.). Samples were incubated overnight at 37° C. in GUS assay buffer.

Herbicide application

To determine herbicide sensitivity of $T_0$ plants and their progeny, a section of leaf blade at the 4 - to 5-leaf stage was painted using a cotton swab with a 0.25% solution (v/v) of Basta™ solution (starting concentration, 200 g/L phophinothricin, Hoechst AG, Frankfurt, Germany) plus 0.1% Tween 20. Plants were scored 1 week after herbicide application.

Genomic DNA isolation, polymerase chain reaction (PCR) and DNA blot hybridization Total genomic DNA from independent calli or leaf tissues was purified as described (Dellaporta, 1993). To test for the presence of uidA in genomic DNA of putatively transformed lines, 250 ng of genomic DNA was amplified,by PCR using the primer set, UIDA1 (5'-agcggccgcaTTACGTCCTGTAGAAACC-3' (SEQ ID NO:9)) and UID2R (5'-agagctcTCATTGTTTGCCTCCCTG-3' (SEQ ID NO:10)); each with a restriction enzyme site (small letters) for subcloning of another DNA construct containing the uidA gene (Cho et al. 1998a;b). The presence of bar was tested using the primer set, BAR5F (5'-CATCGAGACAAGCACGGTCAACTTC-3' (SEQ ID NO:11)) and BAR1R (5'-ATATCCGAGCGCCTCGTGCATGCG-3' (SEQ ID NO:12)) (Lemaux et al. 1996). Amplifications were performed with Taq DNA polymerase (Promega, Madison, Wis.) in a 25-μl reaction (Cho et al. 1998a;b). Twenty-five μl of the PCR product with loading dye was electrophoresed on a 0.8% agarose gel with ethidium bromide and photographed using UV light. Presence of a 1.8-kb fragment with UIDA primers was consistent with an intact uidA fragment; an internal 0.34-kb fragment was produced with BAR primers.

Results

Transient gene expression of globulin-uidA genes

To establish initially the functionality of the maize embryo-specific globulin promoter, plasmids ppGlb1GUS and pdGlbGUS-6 were used in transient assays involving microprojectile bombardment into immature barley endosperm and embryos, respectively. Two controls were included, one negative control bombarded with 1×TE buffer and one positive control bombarded with pAHC25 containing uidA under control of the constitutive maize ubiquitin promoter. GUS driven by the maize embryo-specific globulin promoters was weakly expressed in embryo tissue, but not in endosperm tissue at all. GUS Expression driven by the two globulin promoter uidA fusions was stronger in barley immature embryos with osmotic treatment than without osmotic treatment. The degree of uidA gene expression in embryos driven by the undeleted globulin promoter (1.4-kb, ppGlb1GUS) appeared slightly weaker than that driven by the deleted globulin promoter (0.36-kb, pdGlbGUS-6). ABA treatment enhanced GUS expression in immature embryos without osmotic treament, but not with osmotic treatment. The negative control did not exhibit any GUS expression.

Embryo specific expression in transgenic plants

To further test the maize Glb1-uidA constructs, ten independent stably transformed barley lines were obtained; 5 transformed with the undeleted globulin promoter and another 5 with deleted globulin promoter. Genomic DNA from regenerable transformants was isolated and PCR analysis were performed. Results of PCR amplification of uidA and bar genes from genomic DNA extracted from callus tissues showed that transgenic barley lines resulted in the generation of both the 1.8-kb intact uidA and the 0.34-kb internal bar fragments.

Different tissues from the stable transformants were tested for histochemcal GUS activity. Weak uidA gene expression was exhibited exclusively in embryo tissues transformed with maize Glb1 promoters, but not in the endosperm tisssue. On the other hand, GUS expression under control of the maize ubiquitin (Ubi1) promoter was observed in all tissues; no GUS expression was detected in the negative control.

This invention has been detailed both by example and by description. It should be apparent that one having ordinary skill in the relevant art would be able to surmise equivalents to the invention as described in the claims which follow but which would be within the spirit of the foregoing description. Those equivalents are to be included within the scope of this invention.

TABLE 3

Analysis of $T_0$ barley plants and their progeny transformed with $B_1$-hordein-uidA fusions with and without signal sequence.

| Plasmids used for bombardment | Transgenic Barley Line | DNA uidA | PCR ($T_0$) bar | Basta painting ($T_0$) | GUS activity in $T_1$ seeds (+:−) | Basta resistance in $T_1$ plants (+:−) | Ploidy ($T_0$) | Comments |
|---|---|---|---|---|---|---|---|---|
| pdBhGN1-2 + pAHC20 | GPdBhGN-1 | + | + | + | + (47:25) | + (19:2) | diploid | homozygous |
|  | GPdBhGN-2 | + | + | + | + (11:3) | + (22:10) | tetraploid |  |
|  | GPdBhGN-16 | + | + | + | + (61:31) | + (39:0) | tetraploid |  |
| pdBhssGN5-6 + pAHC20 | GPdBhssGN-7 | + | + | + | + (146:40) | + (38:13) | diploid | homozygous |
|  | GPdBhssGN-10 | + | + | + | + (136:41) | − (0:45) | diploid | homozygous |
|  | GPdBhssGN-23 | + | + | + | + (148:42) | + (7:21) | diploid | homozygous |

REFERENCES

Blake T K, Ullrich S E, Nilan R A (1982) Mapping of the Hor-3 locus encoding D hordein in barley. Theor Appl Genet 63: 367–371

Bradford M M (1976) A rapid and sensitive method for the quantitation of microgram quantities of protein utilizing the principle of protein-dye binding. Anal Biochem 72: 248–254

Brandt A (1976) Endosperm protein formation during kernel development of wild type and a high-lysine barley mutant. Cereal Chem 53: 890–901

Brandt A, Montembault A, Cameron-Mills V, Rasmussen S K (1985) Primary structure of a $B_1$ hordein gene from barley. Carlsberg Res Commun 50: 333–345

Brandt, A., Montembault, A., Cameron-Mills, V. and Rasmussen, S. K. (1985) Primary structure of a B1 hordein gene from barley. *Carlsberg Res. Commun.* 50, 333–345.

Bright S W, Shewry P R (1983) Improvement of protein quality in cereals. CCC Critical Plant Reviews 1: 49–93

Cameron-Mills V (1980) The structure and composition of protein bodies purified from barley endosperm by silica sol density gradients. Carlsberg Res Commun 45: 557–576

Cameron-Mills V, Brandt A (1988) A □-hordein gene. Plant Mol Biol 11: 449–461

Cameron-Mills V, Madrid S M J (1988) The signal peptide cleavage site of a $B_1$ hordein determined by radiosequencing of the in vitro synthesized and processed polypeptide. Carlsberg Res Commun 54:181–192

Cameron-Mills V, Wettstein D von (1980) Protein body formation in the developing barley endosperm. Carlsberg Res Commun 45: 577–594

Cho M-J, Jiang W, Lemaux P G (1998) Transformation of recalcitrant barley genotypes through improvement of regenerability and decreased albinism. Plant Sci (submitted)

Christensen A H, Quail P H (1996) Ubiquitin promoter-based vectors for high-level expression of selectable and/or screenable marker genes in monocotyledonous plants. Transgenic Res 5: 213–218

Dellaporta S (1993) Plant DNA miniprep and microprep. Freeling M, Walbot V (eds) In: Maize Handbook. p 522–525

Entwistle J, Knudsen S, Müller M, Cameron-Mills V (1991) Amber codon suppression: the in vivo and in vitro analysis of two C-hordein genes from barley. Plant Mol Biol 17: 1217–1231

Farrell, L. B. and Beachy, R. N. (1990) Manipulation of □-glucuronidase for use as a reporter in vacuolar targeting studies. *Plant Mol. Biol.* 15, 821–825.

Fiedler U, Conrad U (1995) High-level production and long-term storage of engineered antibodies in trangenic tobacco seeds. Bio/Technol 13: 1090–1093

Forde B G, Heyworth A, Pywell J, Kreis M (1985) Nucleotide sequence of a $B_1$ hordein gene and the identification of possible upstream regulatory elements in endosperm storage protein genes from barley, wheat and maize. Nucl Acids Res 13: 7327–7339

Giese H, Andersen B, Doll H (1983) Synthesis of the major storage protein, hordein, in barley. Pulse-labeling study of grain filling in liquid-cultured detached spikes. Planta 159: 60–65

Higuchi, R. (1990) Recombinant PCR, in *PCR Protocols: A Guide to Methods and Applications* (Innes, M. A., Gelfand, D. H., Sninsky, J. J. and White, T. J., eds.), Academic Press, San Diego, Calif., pp. 177–183.

Horton, M. R., Cai, Z., Ho, S. N. and Pease L. R. (1990) Gene splicing by overlap extension: tailor-made genes using the polymerase chain reaction. *BioTechniques* 8, 528–535.

Hunter C P (1988) Plant regeneration from microspores of barley, *Hordeum vulgare*. PhD thesis. Wye College, University of London, Ashford, Kent Jefferson R A (1987) Assaying chimeric genes in plants. The GUS fusion system. Plant Mol Biol Rep 1: 387–405

Jefferson R A, Kavanagh T A, Bevan M W (1987) GUS fusions: β-glucuronidase as a sensitive and versatile gene fusion marker in higher plants. EMBO J 6: 3901–3907

Jefferson, R. A., Kavanagh, T. A. and Bevan, M. W. (1987) GUS fusions: □-glucuronidase as a sensitive and versatile gene fusion marker in higher plants. *EMBO J.* 6, 3901–3907.

Jensen J, J□rgnesen J H, Jensen H P, Giese H, Doll H (1980) Linkage of the hordein loci Hor1 and Hor2 with the powdery mildew resistance loci Ml-k and Ml-a on barley chromosome 5. Theor Appl Genet 58:27–31

Lefebvre, B., Formstecher, P. and Lefebvre, P. (1995) Improvement of the gene splicing overlap (SOE) method. *BioTechniques* 19, 186–187.

Lemaux P G, Cho M-J, Louwerse J, Williams R, Wan Y (1996) Bombardment-mediated transformation methods for barley. Bio-Rad US/EG Bulletin 2007: 1–6

Lemaux, P. G., Cho, M.-J., Louwerse, J., Williams, R. and Wan, Y. (1996) Bombardment-mediated transformation methods for barley. Bio-Rad US/EG Bulletin 2007, 1–6.

Marris C, Gallois P, Copley J, Kreis M (1988) The 5' flanking region of a barley B hordein gene controls tissue and developmental specific CAT expression in tobacco plants. Plant Mol Biol 10: 359–366

McElroy, D., Chamberlain, D. A., Moon, E. and Wilson, K. J. (1995) Development of gusA reporter gene constructs for cereal transformation: Availability of plant transformation vectors from the CAMBIA Molecular Genetic Resource Service. *Mol. Breeding* 1, 27–37.

Müller M, Knudsen S (1993) The nitrogen response of a barley C-hordein promoter is controlled by positive and negative regulation of the GCN4 and endosperm box. Plant J 4: 343–355

Murashige T, Skoog F (1962) A revised medium for rapid growth and bioassays with tobacco tissue cultures. Physiol Plant 15: 473–497

Murashige, T. and Skoog, F. (1962) A revised medium for rapid growth and bioassays with tobacco tissue cultures. *Physiol. Plant* 15, 473–497.

Pont-Kingdon, G. (1994) Construction of chimeric molecules by a two-step recombinant PCR method. *BioTechniques* 16, 1010–1011.

Rasmussen S K, Brandt A (1986) Nucleotide sequences of cDNA clones for C-hordein polypeptides. Carlsberg Res Commun 51: 371–379

Shewry P R (1993) Barley seed proteins. In barley: Chemistry and technology. Eds A W MacGregor and R S Bahatty, 131–197. St Paul, Minn., Amer Assoc Cereal Chemists, Inc.

Shewry P R, Faulks A J, Pickering R A, Jones I T, Finch R A, Miflin B J (1980) The genetic analysis of barley storage proteins. Heredity 44: 383–389

Shewry P R, Finch R A, Parmer S, Franklin B J (1983) Chromosomal location of Hor3, new locus governing storage proteins in barley. Heredity 50: 179–189

Shewry P R, Parmer S (1987) The HrdF (Hor5) locus encodes □-type hordeins. Barley Genet Newslett 17: 32–35

Sørensen M B, Cameron-Mills V, Brandt A (1989) Transcriptional and post-transcriptional regulation of gene expression in developing barley endosperm. Mol Gen Genet 217: 195–201

Sørensen M B, Müller M, Skerritt J, Simpson D (1996) Hordein promoter methylation and transcriptioal activity in wild-type and mutant barley endosperm. Mol Gen Genet 250: 750–760

Wan Y, Lemaux P G (1994) Generation of large numbers of independently transformed fertile barley plants. Plant Physiol 104: 37–48

We claim:

1. A method for producing seeds containing a selected heterologous protein which is not a seed-storage protein, comprising the steps of:
 (a) stably transforming monocot plant cells with a chimeric gene having:
  (i) a transcriptional regulatory region from the gene of a maturation specific monocot storage protein selected from the group consisting of rice glutelins, rice oryzins, rice prolamines, barley hordeins, oat glutelins, and sorghum kafirins, millet pennisetins, and rye secalins,
  (ii) operably linked to said transcriptional regulatory region, a first DNA sequence encoding a monocot seed-specific N-terminal leader sequence capable of targeting a linked polypeptide to a protein storage body in monocot seeds, and
  (iii) a second DNA sequence encoding such selected non-seed-storage heterologous protein, and linked in translation frame with the first sequence, such that the first and second sequences encode a fusion protein composed of the selected heterologous non-seed-storage protein and an N-terminal leader sequence,
 (b) cultivating plants containing the transformed plant cells under seed-maturation conditions, wherein the expression of the non-seed storage heterologous protein is at least twice that observed with an equivalent chimeric gene lacking the second DNA sequence encoding a monocot seed-specific N-terminal leader sequence, and
 (c) harvesting seeds from the cultivated plants.

2. The method of claim 1, wherein the maturation-specific transcriptional regulatory region is selected from the group consisting of rice glutelin, barley D-hordein, wheat glutenin, and barley $B_1$-hordein promoters.

3. The method of claim 1, wherein the first DNA sequence is the leader sequence associated with a gene selected from the group consisting of rice glutelin, rice globulin, barley D-hordein, and barley $B_1$-hordein.

4. The method of claim 1, wherein the monocot plant is selected from the group consisting of rice, barley, and wheat.

5. The method of claim 1, which further includes isolating the selected proteins from the harvested seeds, by processing the seeds to obtain a fraction enriched for protein-storage bodies, and isolating said protein from the enriched fraction.

* * * * *

UNITED STATES PATENT AND TRADEMARK OFFICE
CERTIFICATE OF CORRECTION

PATENT NO. : 6,642,437 B1
DATED : November 4, 2003
INVENTOR(S) : Peggy G. Lemaux et al.

It is certified that error appears in the above-identified patent and that said Letters Patent is hereby corrected as shown below:

Title page,
Item [75], Inventors, the order of Inventors should read:

-- Myeong-Je Cho, Alameda, CA (US);
Peggy G. Lemaux, Moraga, CA (US);
Bob B. Buchanan, Berkeley, CA (US) --

Signed and Sealed this

Twenty-sixth Day of October, 2004

JON W. DUDAS
*Director of the United States Patent and Trademark Office*

SEQUENCE LISTING

<160> NUMBER OF SEQ ID NOS: 16

<210> SEQ ID NO 1
<211> LENGTH: 486
<212> TYPE: DNA
<213> ORGANISM: Hordeum vulgare
<220> FEATURE:
<221> NAME/KEY: CDS
<222> LOCATION: (430)..(486)

<400> SEQUENCE: 1

| | |
|---|---:|
| aagctttaac aacccacaca ttgattgcaa cttagtccta cacaagtttt ccattcttgt | 60 |
| ttcaggctaa caacctatac aaggttccaa atcatgcaa aagtgatgct aggttgataa | 120 |
| tgtgtgacat gtaaagtgaa taaggtgagt catgcatacc aaacctcggg atttctatac | 180 |
| tttgtgtatg atcatatgca caactaaaag gcaactttga ttatcaattg aaaagtaccg | 240 |
| cttgtagctt gtgcaaccta acacaatgtc caaaatcca tttgcaaaag catccaaaca | 300 |
| caattgttaa agctgttcaa acaaacaaag aagagatgaa gcctggctac tataaatagg | 360 |
| caggtagtat agagatctac acaagcacaa gcatcaaaac caagaaacac tagttaacac | 420 |
| caatccact atg aag acc ttc ctc atc ttt gca ctc ctc gcc att gcg gca | 471 |
|         Met Lys Thr Phe Leu Ile Phe Ala Leu Leu Ala Ile Ala Ala | |
|         1             5            10 | |
| aca agt acg att gca | 486 |
| Thr Ser Thr Ile Ala | |
| 15 | |

<210> SEQ ID NO 2
<211> LENGTH: 19
<212> TYPE: PRT
<213> ORGANISM: Hordeum vulgare

<400> SEQUENCE: 2

Met Lys Thr Phe Leu Ile Phe Ala Leu Leu Ala Ile Ala Ala Thr Ser
1               5                   10                  15

Thr Ile Ala

<210> SEQ ID NO 3
<211> LENGTH: 497
<212> TYPE: DNA
<213> ORGANISM: Hordeum vulgare
<220> FEATURE:
<221> NAME/KEY: CDS
<222> LOCATION: (435)..(497)

<400> SEQUENCE: 3

| | |
|---|---:|
| cttcgagtgc ccgccgattt gccagcaatg gctaacagac acatattctg ccaaaacccc | 60 |
| agaacaataa tcacttctcg tagatgaaga gaacagacca agatacaaac gtccacgctt | 120 |
| cagcaaacag taccccagaa ctaggattaa gccgattacg cggctttagc agaccgtcca | 180 |
| aaaaactgt tttgcaaagc tccaattcct ccttgcttat ccaatttctt ttgtgttggc | 240 |
| aaactgcact tgtccaaccg attttgttct tcccgtgttt cttcttaggc taactaacac | 300 |
| agccgtgcac atagccatgg tccggaatct tcacctcgtc cctataaaag cccagccaat | 360 |
| ctccacaatc tcatcatcac cgagaacacc gagaaccaca aaactagaga tcaattcatt | 420 |
| gacagtccac cgag atg gct aag cgg ctg gtc ctc ttt gtg gcg gta atc | 470 |
|             Met Ala Lys Arg Leu Val Leu Phe Val Ala Val Ile | |
|             1         5          10 | |

```
gtc gcc ctc gtg gct ctc acc acc gct                                  497
Val Ala Leu Val Ala Leu Thr Thr Ala
        15                  20
```

<210> SEQ ID NO 4
<211> LENGTH: 21
<212> TYPE: PRT
<213> ORGANISM: Hordeum vulgare

<400> SEQUENCE: 4

```
Met Ala Lys Arg Leu Val Leu Phe Val Ala Val Ile Val Ala Leu Val
 1               5                  10                  15

Ala Leu Thr Thr Ala
            20
```

<210> SEQ ID NO 5
<211> LENGTH: 41
<212> TYPE: DNA
<213> ORGANISM: Artificial Sequence
<220> FEATURE:
<223> OTHER INFORMATION: Description of Artificial Sequence: PCR primer

<400> SEQUENCE: 5
gcggcaacaa gtacattgca ttacgtcctg tagaaacccc a                    41

<210> SEQ ID NO 6
<211> LENGTH: 42
<212> TYPE: DNA
<213> ORGANISM: Artificial Sequence
<220> FEATURE:
<223> OTHER INFORMATION: Description of Artificial Sequence: PCR primer

<400> SEQUENCE: 6
tggggtttct acaggacgta atgcaatcgt acttgttgcc gc                   42

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence: PCR primer

<400> SEQUENCE: 7
gtaaagcttt aacaacccac acattg                                     26

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: PCR primer

<400> SEQUENCE: 8
cggaattcga tctagtaaca tagatgaca                                  29

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence: PCR primer

<400> SEQUENCE: 9
agcggccgca ttacgtcctg tagaaacc                                   28

```
<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: PCR primer

<400> SEQUENCE: 10
agagctctca ttgtttgcct ccctg                                    25

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: PCR primer

<400> SEQUENCE: 11
catcgagaca agcacggtca acttc                                    25

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: PCR primer

<400> SEQUENCE: 12
atatccgagc gcctcgtgca tgcg                                     24

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence: PCR primer

<400> SEQUENCE: 13
cgcatgcgtg caggtgtatg agtcatt                                  27

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence: PCR primer

<400> SEQUENCE: 14
ccctctagaa gtggattggt gttaact                                  27

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: PCR primer

<400> SEQUENCE: 15
gaagagatga agcctggcta c                                        21

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: PCR primer
```

```
<400> SEQUENCE: 16
cgatccagac tgaatgccca cagg                                                24
```